(12) United States Patent
Liu et al.

(10) Patent No.: US 10,513,475 B2
(45) Date of Patent: Dec. 24, 2019

(54) METHODS AND SYSTEMS FOR CONVERTING HYDROCARBONS

(71) Applicant: ExxonMobil Research and Engineering Company, Annandale, NJ (US)

(72) Inventors: Sophie Liu, Hampton, NJ (US); Jihad M. Dakka, Whitehouse Station, NJ (US); Partha Nandi, Annandale, NJ (US); Sara Yacob, Bridgewater, NJ (US); Quddus A. Nizami, Piscataway, NJ (US); Chuansheng Bai, Phillipsburg, NJ (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 0 days.

(21) Appl. No.: 15/839,974

(22) Filed: Dec. 13, 2017

(65) Prior Publication Data

US 2018/0162789 A1   Jun. 14, 2018

Related U.S. Application Data

(60) Provisional application No. 62/433,833, filed on Dec. 14, 2016.

(51) Int. Cl.
*C07C 2/86* (2006.01)
*C07C 2/62* (2006.01)
(Continued)

(52) U.S. Cl.
CPC ........... *C07C 2/864* (2013.01); *B01J 29/7038* (2013.01); *B01J 29/80* (2013.01); *C07C 1/24* (2013.01);
(Continued)

(58) Field of Classification Search
CPC .. C07C 2/86; C07C 2/62; C07C 31/12; C07C 31/125; C07C 29/50
See application file for complete search history.

(56) References Cited

U.S. PATENT DOCUMENTS

| 3,644,565 A | 9/1968 | Biale |
| 4,384,161 A | 5/1983 | Huang |

(Continued)

FOREIGN PATENT DOCUMENTS

| EP | 0293032 A1 | 11/1988 |
| EP | 0710622 A1 | 5/1998 |
| WO | 9745383 A1 | 12/1997 |

OTHER PUBLICATIONS

Qi et al. (Decomposition of tert-butyl hydroperoxide into tert-butyl alcohol and O2 catalyzed by birnessite-type manganese oxides: Kinetics and activity, 2014, Catalysis Communications, vol. 49, pp. 6-9) (Year: 2014).*

(Continued)

*Primary Examiner* — Youngsul Jeong
(74) *Attorney, Agent, or Firm* — Priya G. Prasad

(57) ABSTRACT

Methods and systems for converting hydrocarbons including exposing a portion of a hydroperoxide-containing feed including tert-butyl hydroperoxide to a solid deperoxidation catalyst under decomposition conditions to form an oxidation effluent comprising tert-butyl alcohol, wherein the solid deperoxidation catalyst comprises a manganese oxide octahedral molecular sieve, are provided herein. Further methods and systems for converting the oxidation effluent to an alkylation product are also provided herein.

14 Claims, 5 Drawing Sheets

(51) Int. Cl.

| | | |
|---|---|---|
| *C07C 29/50* | (2006.01) | |
| *C07C 1/24* | (2006.01) | |
| *C07C 31/12* | (2006.01) | |
| *C07C 31/125* | (2006.01) | |
| *B01J 29/70* | (2006.01) | |
| *C07C 5/02* | (2006.01) | |
| *C07C 29/132* | (2006.01) | |
| *C07C 2/12* | (2006.01) | |
| *C07C 5/03* | (2006.01) | |
| *C07C 5/27* | (2006.01) | |
| *C07C 407/00* | (2006.01) | |
| *C10G 45/58* | (2006.01) | |
| *C10G 50/00* | (2006.01) | |
| *C10G 69/12* | (2006.01) | |
| *C10G 3/00* | (2006.01) | |
| *B01J 29/80* | (2006.01) | |
| *B01J 29/50* | (2006.01) | |

(52) U.S. Cl.
CPC ............... *C07C 2/12* (2013.01); *C07C 2/62* (2013.01); *C07C 5/02* (2013.01); *C07C 5/03* (2013.01); *C07C 5/2702* (2013.01); *C07C 29/132* (2013.01); *C07C 29/50* (2013.01); *C07C 31/12* (2013.01); *C07C 31/125* (2013.01); *C07C 407/00* (2013.01); *C10G 3/49* (2013.01); *C10G 45/58* (2013.01); *C10G 50/00* (2013.01); *C10G 69/126* (2013.01); *B01J 29/50* (2013.01); *C07C 2523/28* (2013.01); *C07C 2523/34* (2013.01); *C07C 2523/889* (2013.01); *C07C 2529/70* (2013.01); *C10G 2300/104* (2013.01); *C10G 2300/1044* (2013.01); *C10G 2300/1081* (2013.01); *C10G 2300/305* (2013.01); *C10G 2400/02* (2013.01)

(56) References Cited

U.S. PATENT DOCUMENTS

| | | | |
|---|---|---|---|
| 4,439,409 A | 3/1984 | Puppe et al. | |
| 4,826,667 A | 5/1989 | Zones et al. | |
| 4,954,325 A | 9/1990 | Rubin et al. | |
| 5,236,575 A | 8/1993 | Bennett et al. | |
| 5,243,084 A | 9/1993 | Cochran et al. | |
| 5,250,277 A | 10/1993 | Kresge et al. | |
| 5,254,518 A | 10/1993 | Soled et al. | |
| 5,304,698 A | 4/1994 | Husain | |
| 5,340,562 A | 8/1994 | O'Young et al. | |
| 5,362,697 A | 11/1994 | Fung et al. | |
| 5,382,731 A | 1/1995 | Chang et al. | |
| 5,414,145 A | 5/1995 | Sheu et al. | |
| 5,510,309 A | 4/1996 | Chang et al. | |
| 5,523,509 A | 6/1996 | O'Young et al. | |
| 5,719,097 A | 2/1998 | Chang et al. | |
| 6,077,498 A | 6/2000 | Diaz et al. | |
| 6,231,751 B1 | 5/2001 | Canos et al. | |
| 6,376,731 B1 | 4/2002 | Evans et al. | |
| 6,756,030 B1 | 6/2004 | Rohde et al. | |
| 7,713,513 B2 | 5/2010 | Jan et al. | |
| 7,842,277 B2 | 11/2010 | Wieslaw et al. | |
| 7,982,084 B1 | 7/2011 | Moscoso et al. | |
| 8,704,023 B2 | 4/2014 | Wieslaw et al. | |
| 8,704,025 B2 | 4/2014 | Wieslaw et al. | |
| 2007/0191662 A1* | 8/2007 | Oikarinen | C07C 2/12 585/533 |
| 2016/0168048 A1* | 6/2016 | Wang | C10L 1/04 585/310 |
| 2018/0162786 A1 | 6/2018 | Dakka et al. | |
| 2018/0162787 A1 | 6/2018 | Dakka et al. | |
| 2018/0162788 A1 | 6/2018 | Dakka et al. | |
| 2018/0162789 A1 | 6/2018 | Liu et al. | |

OTHER PUBLICATIONS

Hajimirzaee (Preparation, modification and characterization of selective zeolite based catalysts for petrochemical applications, Apr. 2015, University of Birmingham) (Year: 2015).*

Feng et al. (Catalytic decomposition of tert-butyl hydroperoxide into tert-butyl alcohol over Me-OMS-1s molecular sieve, CIESC Journal, vol. 66, No. 10, pp. 3965-3970) (Year: 2015).*

Albright et al., "Alkylation of isobutane with C4 olefins 1. First-step reactions using sulfuric acid catalyst", Ind. Eng. Chem. Res., 1988, vol. 27, pp. 381-386.

Corma et al., "Chemistry, Catalysts, and Processes for Isoparaffin-Olefin Alkylation: Actual Situation and Future Trends", Cat. Rev. Sci. Eng., 1993, vol. 35, pp. 483-570.

Feng et al., "Catalytic decomposition of tert-butyl hydroperoxide into tert-butyl alcohol over Me-OMS-1s molecular sieves", J. Chem. Ind. Eng., 2015, vol. 66, pp. 3965-3970.

Hutson, "Phillips HF Alkylation Process for Alkylation of C3, C4, C5 Olefins", Handbook of Petroleum Refining Processes, R.A. Meyers., Ed..

Lin et al., "Decomposition of tert-butyl hydroperoxide into tert butyl alcohol and O2 catalyzed by bimessite-type manganese oxides: Kinetics and activity", Cat. Comm., 2014, vol. 49, pp. 6-9.

Liu et al., "Catalytic Partial Oxidation of Cyclohexane by Bimetallic Ag/Pd Nanoparticles on Magnesium Oxide", Chem. Eur. J..

Luo et al., "One-pot synthesis of MWW zeolite nanosheets using a rationally designed organic structure-directing agent", Chem. Sci., 2015, vol. 6, pp. 6320-6324.

O'Young, "Hydrothermal Synthesis of Manganese Oxides with Tunnel Structures", in Expanded Clays and Other Microporous Structures, vol. II, 333, M.L. Occelli, H.E. Robson Eds. Van Nostrand Reinhold, NY, 1992.

Shah, "UOP HF Alkylation Process", Handbook of Petroleum Refining Processes, R.A. Meyers, Ed., 1986, pp. XX-XX.

The International Search Report and Written Opinion of PCT/US2017/065954 dated Dec. 13, 2017.

The International Search Report and Written Opinion of PCT/US2017/065955 dated Dec. 13, 2017.

The International Search Report and Written Opinion of PCT/US2017/065958 dated Dec. 13, 2017.

The International Search Report and Written Opinion of PCT/US2017/065960 dated Dec. 13, 2017.

* cited by examiner

METHODS AND SYSTEMS FOR CONVERTING HYDROCARBONS

CROSS-REFERENCE TO RELATED APPLICATIONS

This application claims the benefit of provisional U.S. Ser. No. 62/433,833, filed Dec. 14, 2016, the entire contents of which are expressly incorporated by reference herein.

This application is also related to U.S. Ser. No. 15/839,937, filed Dec. 13, 2017, now U.S. Pat. No.10,421,698, and U.S. Ser. No. 15/839,959, also filed Dec. 13, 2017, now U.S. Pat. No. 10,421,699.

FIELD

The present invention relates to systems and methods for converting hydrocarbons including oxidization methods for converting a hydroperoxide to an alcohol and production of alkylate from an isoparaffin feed using such oxidization methods.

BACKGROUND

In conventional petroleum processes, alkylate is typically used to describe a product formed by an alkylation process involving an isoparaffin-containing feed and an olefin-containing feed. Industrially, alkylation reactions often correspond to the reaction of a $C_2$ to $C_5$ olefin, normally 2-butene, with isobutane in the presence of an acidic catalyst to produce a so-called alkylate. This alkylate is a valuable blending component in the manufacture of gasoline due not only to its high octane rating but also to its sensitivity to octane-enhancing additives, especially in light of increasing demand for higher octane and lower Reid Vapor Pressure (RVP) gasoline. Industrial isoparaffin-olefin alkylation processes have historically used hydrofluoric or sulfuric acid catalysts under relatively low temperature conditions. The sulfuric acid alkylation reaction is particularly sensitive to temperature, with low temperatures being favored to minimize the side reaction of olefin polymerization. Acid strength in these liquid acid catalyzed alkylation processes is typically maintained at 88 to 94 weight percent by the continuous addition of fresh acid and the continuous withdrawal of spent acid. The hydrofluoric acid process is less temperature sensitive and the acid is more easily recovered and purified. A general discussion of sulfuric acid alkylation can be found in a series of three articles by L. F. Albright et al., "Alkylation of Isobutane with $C_4$ Olefins", 27 *Ind. Eng. Chem. Res.*, 381-397, (1988). For a survey of hydrofluoric acid catalyzed alkylation, see 1 Handbook of Petroleum Refining Processes 23-28 (R. A. Meyers, ed., 1986). An overview of the entire technology can be found in "Chemistry, Catalysts and Processes of Isoparaffin-Olefin Alkylation—Actual Situation and Future Trends, Corma et al., *Catal. Rev.—Sci. Eng.* 35(4), 483-570 (1993).

Both sulfuric acid and hydrofluoric acid alkylation share inherent drawbacks including environmental and safety concerns, acid consumption, and sludge disposal. Research efforts have, therefore, been directed to developing alkylation catalysts which are equally as effective as, or more effective than, sulfuric or hydrofluoric acids but which avoid many of the problems associated with these two acids.

U.S. Pat. No. 3,644,565 discloses alkylation of a paraffin with an olefin in the presence of a catalyst comprising a Group VIII noble metal present on a crystalline aluminosilicate zeolite having pores of substantially uniform diameter from about 4 to 18 angstrom units and a silica to alumina ratio of 2.5 to 10, such as zeolite Y. The catalyst is pretreated with hydrogen to promote selectivity.

U.S. Pat. No. 4,384,161 describes a process of alkylating isoparaffins with olefins to provide alkylate using a large-pore zeolite catalyst capable of absorbing 2,2,4-trimethylpentane, for example, ZSM-4, ZSM-20, ZSM-3, ZSM-18, zeolite Beta, faujasite, mordenite, zeolite Y and the rare earth metal-containing forms thereof, and a Lewis acid such as boron trifluoride, antimony pentafluoride or aluminum trichloride. The addition of a Lewis acid is reported to increase the activity and selectivity of the zeolite, thereby effecting alkylation with high olefin space velocity and low isoparaffin/olefin ratio.

U.S. Pat. No. 5,304,698 describes a process for the catalytic alkylation of an olefin with an isoparaffin comprising contacting an olefin-containing feed with an isoparaffin-containing feed with a crystalline microporous material selected from the group consisting of MCM-22, MCM-36, and MCM-49 under alkylation conversion conditions of temperature at least equal to the critical temperature of the principal isoparaffin component of the feed and pressure at least equal to the critical pressure of the principal isoparaffin component of the feed.

An additional difficulty with alkylation processes can be related to the availability and/or cost of the feeds for forming alkylate. Light paraffin feeds, such as a feed containing isobutane, are generally considered low cost feeds. However, the corresponding olefin feed for forming alkylate can generally be of higher cost, particularly when the corresponding olefin feed corresponds to a $C_{3+}$ olefin feed, such as a feed of butene or isobutene, because these olefins are typically produced via dehydrogenation reaction which is a high temperature, thermodynamically limited process.

U.S. Pat. No. 5,243,084 describes a process for oxidation of isobutane to tertiary butyl hydroperoxide and tertiary butyl alcohol.

Thus, there remains a need for methods of producing alkylate from light paraffin feeds, which have greater selectively for higher octane rated branched alkanes and which can be produced without the use of liquid acids. Further, there remains a need for selective oxidation methods, which have increased conversion and selectively for producing tertiary alcohols, such as tert-butyl alcohol.

SUMMARY

It has been discovered that oxidation of light paraffin feeds, for example, feeds comprising isobutane, in the presence of oxygen and a solid deperoxidation catalyst comprising a manganese oxide octahedral molecular sieve can produce tertiary alcohols, such as tert-butyl alcohol, with high selectivity and high conversion. Further, after such an oxidation process, the resultant tertiary alcohols can be converted to high octane alkanes without the use of liquid acids by methods including conversion of the tertiary alcohol to an alkylate product via dehydration, dimerization and hydrogenation in the presence of at least one solid acid catalyst.

In various aspects, a method for converting hydrocarbons is provided. The method can include an oxidizing step comprising exposing a portion of a hydroperoxide-containing feed comprising tert-butyl hydroperoxide to a solid deperoxidation catalyst under decomposition conditions to form an oxidation effluent comprising tert-butyl alcohol. The solid deperoxidation catalyst can comprises a manganese oxide octahedral molecular sieve.

In some aspects, the decomposition conditions can comprise a temperature of about 50° C. to about 170° C. and a pressure of about 10 psig to about 500 psig.

In some aspects, at least about 70% or at least about 90% of the tert-butyl hydroperoxide can be converted to tert-butyl alcohol and/or the solid deperoxidation catalyst has a selectivity of at least about 70% or at least about 90% for conversion of tert-butyl hydroperoxide to tert-butyl alcohol.

In some aspects, the oxidizing step can further comprise exposing an isoparaffin-containing feed comprising isobutane to oxidation conditions in the presence of oxygen to form the hydroperoxide-containing product. At least about 10 wt % of the isobutane in the isoparaffin-containing feed can be converted to tert-butyl alcohol. In some aspects, the isoparaffin-containing feed can optionally comprise at least about 80 wt % isobutane relative to a weight of the isoparaffin-containing feed.

In some aspects, the oxidation conditions can comprise a temperature of about 100° C. to about 200° C. and a pressure of about 200 psig to about 1000 psig.

In some aspects, a portion of the oxidation effluent can further comprise water, one or more oxygenates, or a combination thereof, and the one or more oxygenates optionally comprises water, methanol, an ester, acetone, or a combination. In some aspects, the ratio by weight of tert-butyl alcohol to methanol in the oxidation effluent can be from about 10:1 to about 25:1, the ratio by weight of tert-butyl alcohol to acetone can be from about 4:1 to about 20:1, or both. In some aspects, the oxidation effluent can comprise a molar ratio of isobutane to tert-butyl alcohol of about 0:1 to about 2:1.

In some aspects, the method can further include a dehydrating and/or dimerizing step comprising exposing a portion of the oxidation effluent to a first solid acid catalyst under dehydrating and/or dimerizing conditions to form an isoolefin-containing effluent comprising 2,4,4-trimethylpent-1-ene and/or 2,4,4-trimethylpent-2-ene. At least about 70 wt % of tert-butyl alcohol can be converted to 2,4,4-trimethylpent-1-ene and/or 2,4,4-trimethylpent-2-ene. In some aspects, the method can further include a hydrogenating step comprising exposing a portion of the isoolefin-containing effluent to a second solid acid catalyst and hydrogen under hydrogenation conditions to form an alkylation effluent. The alkylation effluent can comprise a $C_8$ fraction comprising at least 50 wt % or at least 70 wt % of 2,3,4-, 2,3,3- and 2,2,4-trimethylpentane having an octane rating, as determined by (RON+MON)/2, of at least about 90 or at least about 95 or about 100, relative to a weight of the $C_8$ fraction.

In some aspects, the dehydration and dimerization conditions can comprise a temperature about 100° C. to about 210° C.

In some aspects, the method can further include one or more of: exposing an n-paraffin-containing feed comprising n-butane to a bifunctional acid catalyst to form the isoparaffin-containing feed via isomerization; separating a portion of n-butane and/or isobutane from the alkylation effluent to form a first recycle stream; separating a portion of n-butane and/or isobutane from the oxidation effluent to form a second recycle stream; and recycling a portion of the first recycle stream and/or the second recycle stream to the n-paraffin-containing feed and/or the isoparaffin-containing feed.

In various aspects, an alkylate produced according to the methods described herein is provided.

In various aspects, a system for conversion of hydrocarbons is provided. The system can include a hydroperoxide feed stream comprising tert-butyl hydroperoxide and an oxidation effluent stream comprising tert-butyl alcohol. The system can further include an oxidation reaction zone comprising a hydroperoxide feed inlet, an oxidation effluent outlet, and a solid deperoxidation catalyst comprising a manganese oxide octahedral molecular sieve. The solid deperoxidation catalyst can have a selectivity of at least about 70% for conversion of tert-butyl hydroperoxide to tert-butyl alcohol. The hydroperoxide feed stream and the oxidation effluent stream can be in fluid communication with the oxidation reaction zone.

In some aspects, the system can further include an isoparaffin feed stream comprising isobutane and an oxygen stream. The oxidation reaction zone can further comprise a first oxidation reactor comprising an isoparaffin feed inlet, an oxygen inlet, and a hydroperoxide feed stream outlet. The isoparaffin feed stream, the oxygen stream, and the hydroperoxide feed stream can be in fluid communication with the first oxidation reactor. In some aspects, the oxidation reaction zone can further comprise a second oxidation reactor comprising the solid deperoxidation catalyst, the hydroperoxide feed inlet, and the oxidation effluent outlet. The hydroperoxide feed stream and the oxidation effluent stream can be in fluid communication with the second oxidation reactor.

In some aspects, the system can further include an isoolefin effluent stream comprising 2,4,4-trimethylpent-1-ene and/or 2,4,4-trimethylpent-2-ene and a dehydration and dimerization reaction zone comprising an oxidation effluent inlet, an isoolefin effluent outlet, and a first solid acid catalyst. The oxidation effluent stream and the isoolefin effluent stream can be in fluid communication with the dehydration and dimerization reaction zone. In some aspects, the system can further include a hydrogen stream, an alkylation effluent stream and a hydrogenation zone comprising an isoolefin effluent inlet, an alkylation effluent outlet, and a second solid acid catalyst. The isoolefin effluent stream, the hydrogen stream, and the alkylation effluent stream can be in fluid communication with the hydrogenation reaction zone.

In some aspects, the alkylation effluent stream can comprise a $C_8$ fraction comprising at least 50 wt % or at least 70 wt % of 2,3,4-, 2,3,3- and 2,2,4-trimethylpentane having an octane rating, as determined by (RON+MON)/2, of at least about 90, or at least about 95, or about 100, relative to a weight of the $C_8$ fraction.

In some aspects, the dehydration and dimerization reaction zone and the hydrogenation reaction zone can be present in different vessels or in the same vessel.

In some aspects of the methods and systems described herein, the manganese oxide octahedral molecular sieve can comprises $MnO_6$ octahedra which share edges to form a tunnel structure. In some aspects, the tunnel structure can be a 2×2 tunnel structure or a 3×3 tunnel structure.

In some aspects of the methods and systems described herein, the solid deperoxidation catalyst can be selected from the group consisting of OMS-2, Nb-OMS-2, K-OMS-2, OMS-1, amorphous manganese oxide and a combination thereof.

In some aspects of the methods and systems described herein, the first solid acid catalyst and the second solid acid catalyst can be the same or different. In some aspects, the first and/or second solid acid catalyst can comprise a zeolite, a mixed metal oxide, or a combination thereof. For example, the first and/or second solid acid catalyst can comprise a crystalline microporous material of the MWW framework type. More generally, a crystalline microporous material of the MWW framework type can optionally be selected from the group consisting of MCM-22, PSH-3, SSZ-25, ERB-1, ITQ-1, ITQ-2, MCM-36, MCM-49, MCM-56, EMM-10, EMM-12, EMM-13, UZM-8, UZM-8HS, UZM-37, MIT-1, and a mixture thereof. Optionally, an MWW framework type material can contain up to 10% by weight of impurities of other framework structures.

In aspects of the methods and systems described herein, the first and/or second solid acid catalyst comprises a mixed metal oxide based on oxides of Fe/W/Zr, W/Zr, Ce/W/Zr, Cu/W/Zr, Mn/W/Zr, or a combination thereof. The first and/or second solid acid catalyst can further comprises an inorganic oxide binder. Optionally, the inorganic oxide binder can comprise alumina, silica or a combination thereof or the inorganic oxide binder can be substantially free of amorphous alumina. Optionally, the inorganic oxide binder can comprise silica.

Other embodiments, including particular aspects of the embodiments summarized above, will be evident from the detailed description that follows.

DETAILED DESCRIPTION OF THE INVENTION

I. Overview

Figure 1:
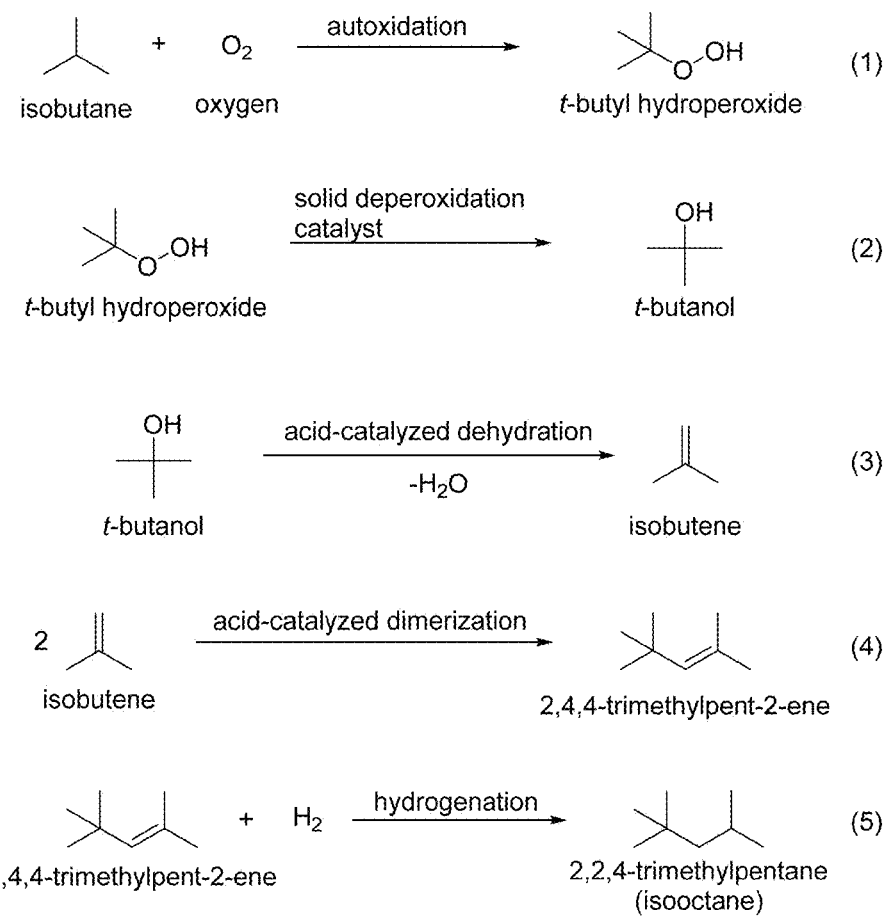
FIG. 1 shows an example of a five-step reaction scheme for forming alkylate from isoparaffins including a two-step oxidation of a portion of the isoparaffins to form alcohols.

In various aspects, systems and methods are provided for converting hydrocarbons (e.g., via decomposition) including oxidation methods for converting a hydroperoxide, such as tert-butyl hydroperoxide, to an alcohol, such as tert-butyl alcohol. In some aspects, the selective oxidation can include two steps, for example, conversion of a portion of isoparaffins into a hydroperoxide, such as isobutane to tert-butyl hydroperoxide, followed by decomposition of the hydroperoxide in the presence of a solid deperoxidation catalyst to an alcohol, such as tert-butyl hydroperoxide to tert-butyl alcohol. It has been unexpectedly discovered that a solid deperoxidation catalyst, such as a manganese oxide octahedral molecular sieve, can convert the hydroperoxide to alcohol with high conversion and selectivity. In various aspects, systems and methods are also provided for forming alkylate from an isoparaffin-containing feed, for example, containing isobutane, utilizing such oxidation methods and without the use of liquid acids. Following oxidation of an isoparaffin-containing feed to an alcohol, the alcohol can then be converted to an alkylate product including high octane alkanes via dehydration, dimerization and hydrogenation in the presence of at least one solid acid catalyst. It has also been unexpectedly discovered that a solid acid catalyst can facilitate conversion of tertiary alcohols to alkylate product under less severe conditions even in the presence of water because the solid acid catalyst can tolerate water. A catalyst having an MWW framework is an example of a suitable solid acid catalyst.

II. Methods for Converting Hydrocarbons

Oxidizing Step

Methods for converting hydrocarbons including an oxidizing step are provided herein. The oxidizing step can comprise exposing a portion of a hydroperoxide-containing feed to a solid deperoxidation catalyst under decomposition conditions to form an oxidation effluent comprising an alcohol. In various aspects, the decomposition conditions, for example in an oxidation reaction zone, reaction stage, or reactor can include, for example, a reaction temperature of about 50° C. to about 170° C. or about 50° C. to about 100° C., a pressure of about 10 psig (~0.069 MPag) to about 500 psig (~3.4 MPag), and a residence time in the oxidation zone of about 1 hour to about 15 hours.

The hydroperoxide-containing feed can correspond to a feed including tert-butyl hydroperoxide, $C_{4+}$ hydroperoxides, $C_{5+}$ hydroperoxides, $C_4$-$C_6$ hydroperoxides, or $C_4$-$C_5$ hydroperoxides. In some aspects, the hydroperoxide-containing feed can contain, relative to a weight of the hydroperoxide-containing feed, at least about 10 wt % of hydroperoxides (and up to 100 wt %), or at least about 20 wt %, or at least about 40 wt %, or at least about 60 wt %, or at least about 80 wt % or at least about 90 wt %, or at least about 95 wt %, or at least about 99 wt %, such as a feed that substantially contains hydroperoxides (i.e., about 99.5 wt % or higher) or about 10 wt % to about 100 wt %, or about 20 wt % to about 90 wt % or about 40 wt % to about 80 wt %. In some aspects, the hydroperoxide-containing feed can correspond to a tert-butyl hydroperoxide-containing feed that contains, relative to a weight of the tert-butyl hydroperoxide-containing feed, at least about 10 wt % of tert-butyl hydroperoxide (and up to 100 wt %), or least about 20 wt %, or at least about 40 wt %, or at least about 60 wt %, or at least about 80 wt %, or at least about 90 wt %, or at least about 95 wt %, or at least about 99 wt %, such as a feed that substantially contains tert-butyl hydroperoxide (i.e., about 99.5 wt % or higher) or about 10 wt % to about 100 wt %, or about 20 wt % to about 90 wt %, or about 40 wt % to about 80 wt %. In various aspects, other components present in the hydroperoxide-containing feed (such as a tert-butyl hydroperoxide-containing feed) can include n-paraffins, isoparaffins, oxygen, and/or cycloparaffins, and/or less than about 2 wt % of compounds typically present due to the nature of a process that generated the hydroperoxide-containing feed.

As discussed above, it has been unexpectedly discovered that a solid deperoxidation catalyst, such as a manganese oxide octahedral molecular sieve, can convert the hydroperoxide to alcohol with high conversion and selectivity. Suitable manganese oxide octahedral molecular sieves comprise $MnO_6$ octahedra which share edges to form a three-dimensional framework tunnel structure which may have exchangeable metal cations present in the tunnels (tunnel cations). The tunnel structures can be mono-directional and of varying sizes.

In various aspects, the tunnel structure can be composed of $MnO_6$ octahedra which share edges to form double chains, and the octahedra of the double chains share corners with adjacent double chains to form a 2×2 tunnel structure, such as is present in the naturally occurring manganese mineral hollandite. Such a 2×2 tunnel structure molecular sieve can have generally square cross-section pores with the sides of the square being about 4.6 Å in length or having a one-dimensional pore diameter of 4.6 Å. Typically, these materials can have a surface area between 120-380 m²/g and little internal pore volume, typically less than 10% of the surface area may be from the internal pores. Examples of hollandite species include, but are not limited to hollandite (BaMn$_8$O$_{16}$), cryptomelane (KMn$_8$O$_{16}$), manjiroite (NaMn$_8$O$_{16}$) and coronadite (PbMn$_8$O$_{16}$). Synthetic manganese oxide octahedral molecular sieves having 2×2 tunnel structures are referred to in the art by the designation OMS-2. Alternatively, the manganese oxide octahedral molecular sieves may have a 3×3 tunnel structure with larger pores corresponding to natural occurring manganese mineral todorokite formed by triple chains of MnO$_6$ edge-sharing octahedra. Synthetic manganese oxide octahedral molecular sieves having 3×3 tunnel structures are referred to in the art by the designation OMS-1. Alternatively, the manganese oxide octahedral molecular sieves may have a 4×4 tunnel structure. Synthetic manganese oxide octahedral molecular sieves having 4×4 tunnel structures are referred to in the art by the designation OMS-3. The manganese oxide octahedral molecular sieves employed in the present oxidizing step can be produced by any of the synthesis methods known in the art. For example, OMS-2 (2×2 tunnel structure) MnO molecular sieves can be produced by the methods described in "Hydrothermal Synthesis of Manganese Oxides with Tunnel Structures," in Synthesis of Microporous Materials, Vol. II, 333, M. L. Occelli, H. E. Robson Eds. Van Nostrand Reinhold, NY, 1992, whereas OMS-1 (3×3 tunnel structure) materials can be produced by the methods described in U.S. Pat. Nos. 5,340,562 and 5,523,509, and OMS-3 (4×4 tunnel structure) materials by the methods described in EP-A-0710622, the entire contents of all of which are incorporated herein by reference.

The manganese oxide octahedral molecular sieves employed herein typically may comply with the general formula (I):

$$[A_{16-a}M_aMn_{16-a}O_{32}]_n \quad (I)$$

wherein:
A can represent a tunnel cation that may be in oxidation state +1, +2, +3, +4 or +5, wherein the metal of the cation is selected from the transition metals (Groups 3-12) and metals of Group 1 and Group 2 of the IUPAC Periodic Table of the Elements;
M can represent a lattice cation that may be in oxidation state +1, +2, +3, +4 or +5, wherein the metal of the cation is a transition metal (Groups 3-12) other than manganese;
Mn represents manganese;
a can be a number equal to or greater than zero and less than 16, preferably in the range of 0.1 to <16; and
n is a number equal to or greater than 1.

Additionally or alternatively, the manganese oxide octahedral molecular sieve may be hydrated, that is, it may have one or more H$_2$O molecules associated with the general formula (I). Alternatively, the manganese oxide octahedral molecular sieve may be dehydrated, such as, by heating at a temperature of at least 200° C., before being used in the present oxidizing step.

It is contemplated herein that in the general formula (I), where there is more than one tunnel cation A then each A may be the same or different with regard to oxidation state and/or metal. Similarly, where the composition contains more than one lattice cation M, then each M may be the same or different with regard to oxidation state and/or metal. Suitable metals for the tunnel cations A include potassium, sodium, cesium, barium, magnesium, silver, copper, and niobium. Suitable metals for the lattice cations M include magnesium, cobalt, nickel copper and zinc. It will be appreciated that the tunnel cations A, but not the lattice cations M, can generally be replaced by conventional ion exchange techniques.

In various aspects, the solid deperoxidation catalyst may be OMS-2 or X-OMS-2, where X may be a transition metal (Groups 3-12) and a metal of Group 1 and Group 2 of the IUPAC Periodic Table of the Elements Group. For example, a solid deperoxidation catalyst may be Nb-OMS-2 or K-OMS-2. In further aspects, a solid deperoxidation catalyst may be selected from the group consisting of OMS-2, Nb-OMS-2, K-OMS-2, OMS-1, amorphous manganese oxide and a combination thereof.

Other suitable solid deperoxidation catalysts include, but are not limited to other metal containing molecular sieve materials, such as a metal-containing APO and a metal-containing zeolite. Examples of such metals include, but are not limited to V, Ce, Cr, and Co. In some embodiments, a solid deperoxidation catalyst can be selected from the group consisting of OMS-2, Nb-OMS-2, K-OMS-2, OMS-1, amorphous manganese oxide, a Ce molecular sieve, Cr-APO, Co-APO, V-zeolite, and a combination thereof Without being bound by theory, it is believed that this oxidizing step may proceed by a radical propagation mechanism in the presence of the solid deperoxidation catalyst whereby the decomposition of tert-butyl hydroperoxide can result in the formation of tert-butoxy radicals that may abstract a hydrogen atom from tert-butyl hydroperoxide and/or isobutane, which may produce tert-butyl alcohol, a tertiary tert-butyl radical, and/or a tert-butylperoxy radical. The terty-butyl radical may react with molecular dioxygen (O$_2$) to form a tert-butylperoxy radical. The tert-butylperoxy radical can also abstract a hydrogen atom from isobutane to form tert-butyl hydroperoxide and another tert-butyl radical, and these products may react as previously described to produce tert-butyl alcohol. Additionally or alternatively, two tert-butylperoxy radicals may dimerize to form R—O—O—O—O—R (R=tert-butyl), which may decompose to two tert-butoxy radicals and molecular dioxygen.

In various aspects, the oxidation effluent can correspond to an effluent including tert-butyl alcohol, C$_{4+}$ alcohols, C$_{5+}$ alcohols, C$_4$-C$_6$ alcohols, or C$_4$-C$_5$ alcohols. In some aspects, the oxidation effluent can contain, relative to a weight of the oxidation effluent, at least about 10 wt % of alcohols (and up to 90 wt %), or at least about 20 wt %, or at least about 30 wt %, or at least about 40 wt %, or at least about 50 wt %, or at least about 60 wt %, or at least about 70 wt %, or at least about 80 wt % or at least about 85 wt % or about 10 wt % to about 90 wt %, or about 20 wt % to about 80 wt % or about 40 wt % to about 70 wt %. In some aspects, the oxidation effluent can correspond to a tert-butyl alcohol-containing effluent that contains, relative to a weight of the tert-butyl alcohol-containing effluent, at least about 10 wt % of tert-butyl alcohol (and up to 90 wt %), or at least about 20 wt %, or at least about 30 wt %, or at least about 40 wt %, or at least about 50 wt %, or at least about 60 wt %, or at least about 70 wt %, or at least about 80 wt % or at least about 85 wt % or about 10 wt % to about 90 wt %, or about 20 wt % to about 80 wt % or about 40 wt % to about 70 wt %.

In various aspects, other components may be present in the oxidation effluent, for example, the oxidation effluent may further comprise one or more oxygenates, isoparaffins (e.g., isobutane) or a combination thereof. The one or more oxygenates may be water, an additional alcohol, such as methanol, an ester, acetone, or a combination thereof. In some aspects, the oxidation effluent can contain, relative to a weight of the oxidation effluent, ≤about 50 wt % of these additional components, singularly or in combination, (and as low as 0.0 wt %), or ≤about 40 wt %, or ≤about 30 wt %, or ≤about 20 wt %, or ≤about 10 wt %, or ≤about 5.0 wt %, or ≤about 1.0 wt %, or ≤about 0.10 wt %, or about 0.0 wt % to about 50 wt %, or about 0.10 wt % to about 40 wt % or about 1.0 wt % to about 30 wt %. In some aspects, a ratio by weight of tert-butyl alcohol to methanol in the oxidation effluent can be from about 8:1 to about 200:1, or about 8:1 to about 100:1, or about 10:1 to about 150:1, or about 20:1 to about 100:1, or about 10:1 to about 25:1, or about 20:1 to about 25:1. Additionally or alternatively, a ratio by weight of tert-butyl alcohol to acetone in the oxidation effluent can be from about 5:1 to about 200:1, or about 5:1 to about 100:1, or about 5:1 to about 50:1, or about 8:1 to about 200:1, or about 8:1 to about 100:1, or about 8:1 to about 50:1, or about 8:1 to about 13:1, or about 4:1 to about 20:1, or about 10:1 to about 150:1.

Advantageously, during the oxidizing step described herein employing the solid deperoxidation catalyst described herein, a hydroperoxide, such as tert-butyl hydroperoxide can be converted to an alcohol, such as tert-butyl alcohol, with high conversion and selectivity. For example, at least about 50% (and up to 100%) of the hydroperoxide (e.g., tert-butyl hydroperoxide) can be converted to an alcohol (e.g., terty-butyl alcohol), or at least about 60%, or at least about 70%, or at least about 80%, or at least about 90%, or at least about 95%, or at least about 99%, or about 50% to about 100%, or about 80% to about 100%, or about 90% to about 100%. Additionally or alternatively, the solid deperoxidation catalyst can have a selectivity for conversion of a hydroperoxide (e.g., tert-butyl hydroperoxide) to an alcohol (e.g., tert-butyl alcohol) of at least about 50% (and up to 100%), or at least about 60%, or at least about 70%, or at least about 80%, or at least about 90%, or at least about 95%, or at least about 99%, or about 50% to about 100%, or about 80% to about 100%, or about 90% to about 100%.

In various aspects, the oxidizing step may further comprise exposing an isoparaffin-containing feed, for example comprising isobutane, to oxidation conditions in the presence of oxygen to form the hydroperoxide-containing feed as described herein. It is contemplated herein that the step of exposing an isoparaffin-containing feed to oxidation conditions in the presence of oxygen and the step of exposing a portion of a hydroperoxide-containing feed to a solid deperoxidation catalyst under decomposition conditions can be both performed in the same or different reactors.

The oxidation of isobutane (and/or other $C_5$-$C_6$ isoparaffins) can be performed by any convenient known oxidation method. The isoparaffin-containing feed can correspond to a feed including isobutane, $C_{4+}$ isoparaffins, $C_{5+}$ isoparaffins, $C_4$-$C_5$ isoparaffins, or $C_4$-$C_6$ isoparaffins. In some aspects, the isoparaffin-containing feed can contain, relative to a weight of the isoparaffin-containing feed, at least about 80 wt % of isoparaffins (and up to 100 wt %), or at least about 90 wt %, or at least about 95 wt %, or at least about 99 wt %, such as a feed that substantially contains isoparaffins (i.e., about 99.5 wt % or higher). In some aspects, the isoparaffin-containing feed can correspond to an isobutane-containing feed that contains, relative to a weight of the isoparaffin-containing feed, at least about 80 wt % of isobutane (and up to 100 wt %), or at least about 90 wt %, or at least about 95 wt %, or at least about 99 wt %, such as a feed that substantially contains isobutane (i.e., about 99.5 wt % or higher). In various aspects, other components present in the isoparaffin-containing feed (such as an isobutane-containing feed) can include n-paraffins, cycloparaffins, and/or less than about 2 wt % of compounds typically present due to the nature of a process that generated the isoparaffin feed.

In various aspects, at least about 10% (and up to 100%) of the isoparaffin (e.g., isobutane) can be converted to an alcohol (e.g., terty-butyl alcohol), or at least about 20%, or at least about 30%, or at least about 40%, or at least about 50%, or at least about 60%, or at least about 70%, or at least about 80%, or at least about 90%, or at least about 95%, or at least about 99%, or about 10% to about 100%, or about 50% to about 100%, or about 80% to about 100%.

As an example, isobutane can be reacted with oxygen in a reactor to produce a mixture of t-butyl hydroperoxide along with t-butyl alcohol. The isobutane oxidation reaction conditions in the oxidation reactor can include, for example, a reaction temperature of about 100° C. to about 200° C., a pressure of about 200 psig (~1.4 MPag) to about 1000 psig (~6.9 MPag) or about 200 psig (~1.4 MPag) to about 500 psig (~3.4 MPag), and a residence time in the oxidation zone of about 1 hour to about 15 hours. Oxygen can be used as the oxidant, although minor amounts of nitrogen and/or other inert gases can also be present.

Overall, the above reaction conditions can generate a weight ratio of t-butyl alcohol to t-butyl hydroperoxide in the liquid phase of about 0.8. Due to the higher vapor pressure of t-butyl alcohol, withdrawing the vapor above the reaction zone can result in a gas phase product with a weight ratio of t-butyl alcohol to t-butyl hydroperoxide of roughly 1.0. This can be facilitated, for example, by operating the oxidation reactor to maintain the reaction mixture at or near the boiling point. The withdrawn vapor can also include, for example, unreacted isobutane and other additional reaction side products. These additional reaction products can include, for example, water and oxygenate impurities, such as methanol and acetone. Depending on the nature of the fractionation, the ratio of t-butyl alcohol to t-butyl hydroperoxide can be further increased. In some aspects, a fraction enriched in t-butyl hydroperoxide can be returned to the oxidation reactor. For a fraction containing t-butyl alcohol, the fraction can optionally be exposed to elevated temperatures of about 100° C. to about 200° C. for additional time to allow for further decomposition of t-butyl hydroperoxide to t-butyl alcohol. Without being bound by any particular theory, it is believed that forming alcohols from isoparaffins by oxidation as described herein can provide a method for alcohol formation under lower severity conditions in comparison with processes such as high temperature reforming. This can allow the conditions for formation of alcohol to be more similar to the eventual conditions for further alkylate formation. Additionally or alternately, it is believed that the selectivity of alcohol formation can be improved relative to a high temperature reforming process.

In some embodiments, for alkylate formation, a desirable oxidation effluent fraction from an oxidation process can have a molar ratio and/or volume ratio of isoparaffin (e.g., isobutane) to alcohol (e.g., tert-butyl alcohol) of about 5:1 to about 200:1, or about 5:1 to about 100:1, or about 10:1 to about 100:1, or about 10:1 to about 40:1. This can correspond to, for example, conversion of at least about 0.5 wt % of the isobutane under the oxidation conditions, or at least about 1.0 wt %. Alternatively, the conversion of isoparaffin (e.g., isobutane) to alcohol (e.g., tert-butyl alcohol) may be higher, for example, a molar ratio and/or volume ratio of isoparaffin (e.g., isobutane) to alcohol (e.g., tert-butyl alcohol) can be about 0:1 to about 20:1; about 0:1 to about 2:1, or about 1:1 to about 10:1. In various aspects, at least about 10% (and up to 100%) of the isoparaffin (e.g., isobutane) can be converted to an alcohol (e.g., terty-butyl alcohol), or at least about 20%, or at least about 30%, or at least about 40%, or at least about 50%, or at least about 60%, or at least about 70%, or at least about 80%, or at least about 90%, or at least about 95%, or at least about 99%, or about 10% to about 100%, or about 50% to about 100%, or about 80% to about 100%. In some aspects, a fraction generated by the isobutane oxidation reaction may have a suitable ratio of tert-butyl alcohol to isobutane. In other aspects, a product fraction from the isobutane oxidation reaction can be blended with additional isobutane to form a feed for alkylate formation.

It is noted that other isoparaffins can potentially be oxidized to generate tertiary alcohols. For example, an isopentane or isohexane feed could be oxidized to generated tertiary alcohols. This could be useful, for example, if an available source of isoparaffins includes a mixture of $C_{4+}$ isoparaffins. While use of higher carbon number isoparaffins could lead to formation of compounds during alkylation that are above the traditional naphtha boiling range for gasoline formation, such heavier compounds can be readily separated by boiling point separation and used as part of a distillate fuel fraction.

Another potential difficulty with $C_{5+}$ isoparaffins is that such isoparaffins contain multiple types of carbon sites. Isobutane corresponds to an isoparaffin with three primary (i.e., terminal) carbons and one tertiary carbon. When isobutane is oxidized, the selectivity for forming t-butyl alcohol is high, as the primary carbons have only a limited ability to stabilize the reaction intermediates that could allow for formation of an alcohol. Additionally, once t-butyl alcohol is formed, little or no transfer of the alcohol from the tertiary carbon to a primary carbon would be expected. By contrast, an isopentane (such as 2-methylbutane) includes 3 primary carbons, a tertiary carbon, and a secondary carbon. While the tertiary carbon is the most favorable location for formation of an alcohol, the secondary carbon can also be a suitable location. As a result, oxidation of a $C_{5+}$ isoparaffin can typically result in formation of a mixture of alcohols. Additionally, the presence of multiple non-primary carbons can also facilitate migration of the alcohol group after formation and/or migration of the double bond in the resulting in-situ olefin. As a result, using alcohols formed from $C_{5+}$ paraffins can tend to lead to production of a larger mixture of alkylate products, as opposed to the relatively high selectivity for formation of tri-methylpentanes that is exhibited when isobutane is used as the feed for oxidation. Because tri-methylpentanes can have a relatively high octane value, the formation of a wider variety of products when using $C_{5+}$ isoparaffins can tend to reduce the octane value of the resulting alkylate.

Before being sent to other reactors, the isoparaffin feed and/or the oxidation product fraction containing the tertiary alcohol may be treated to remove catalyst poisons e.g., using guard beds with specific absorbents for reducing the level of S, N, and/or organic acids to values which do not affect catalyst stability activity and selectivity. It is noted that the process described herein can be conducted in any known reactor, including reactors which allow for continuous or semi-continuous catalyst regeneration, such as fluidized and moving bed reactors, as well as swing bed reactor systems where multiple reactors are oscillated between on-stream mode and regeneration mode. Alternatively, simple fixed bed reactors (including trickle-bed reactors), without swing bed capability can be utilized. In such cases, cycle lengths (on-stream times between successive catalyst regenerations) in excess of 150 days may be obtained.

Dehydrating, Dimerizing and Hydrogenating Steps

In various aspects, oxidation effluent of isobutane and tert-butyl alcohol can be formed based on generation of t-butyl alcohol as described above. This oxidation effluent may be used as a feed for production of an alkylate or alkylation effluent via dehydrating, dimerizing and hydrogenating steps where the tert-butyl alcohol (and/or other tertiary alcohol) can be substantially quantitatively converted to olefin in the presence of a solid acid catalyst, and the resulting olefins can then react to form alkylate in the presence of the solid acid catalyst.

Thus, in various aspects, the method may further comprise a dehydrating and/or dimerizing step comprising exposing a portion of the oxidation effluent to a first solid acid catalyst under dehydrating and/or dimerizing conditions to form an isoolefin-containing effluent. It is contemplated herein, that the dehydrating step and the dimerizing step can be performed separately or together in the same or different vessels or reactors. During the dehydrating step, a portion of the alcohol (e.g., tert-butyl alcohol) in the oxidation effluent may be converted to an alkene, such as isobutene by exposing the oxidation effluent to the first solid acid catalyst. During the dimerizing step, two of the alkenes (e.g., isobutene) produced can dimerize in the presence of a first solid acid catalyst to produce the isoolefin-containing effluent. In some aspects, the method may further comprise a hydrogenating step comprising exposing a portion of the isoolefin-containing effluent to a second solid acid catalyst and hydrogen under hydrogenation conditions to form an alkylation effluent.

In various aspects, the first solid acid catalyst and the second solid acid catalyst can be the same or different. Solid acid catalysts can generally refer to solid materials that can provide acidic sites for catalysis of reactions. Some examples of solid acid catalysts can include various types of zeolites and/or molecular sieves. For example, in zeolitic structures that include silicon and aluminum in the framework, the aluminum atoms can potentially serve as acidic catalysis sites. Suitable zeolitic materials for use as solid acid catalysts can include ZSM-4, ZSM-20, ZSM-3, ZSM-18, zeolite Beta, faujasite, mordenite, zeolite Y and the rare earth metal-containing forms thereof. More generally, crystalline materials having a porous framework structure built from tetrahedra atoms connected by bridging oxygen atoms can potentially be suitable solid acid catalysts. This can include aluminosilicates having a zeolitic framework as well as crystalline structures containing oxides of heteroatoms different from silicon and aluminum. Such heteroatoms can include any heteroatom generally known to be suitable for inclusion in a zeolitic framework, such as gallium, boron, germanium, phosphorus, zinc, and/or other transition metals that can substitute for silicon and/or aluminum in a zeolitic framework Still other examples of solid acid catalysts can include mixed metal oxides. Examples of suitable mixed metal oxides can include mixed metal oxides based on oxides of Fe/W/Zr, W/Zr, Ce/W/Zr, Cu/W/Zr, and/or Mn/W/Zr. In various aspects, the first and/or second solid acid catalyst may comprise a zeolite, a mixed metal oxide or a combination thereof.

Suitable solid acid catalysts employed herein may have an MWW framework type. An MWW framework catalyst corresponds to a catalyst including a crystalline microporous material of the MWW framework type. As used herein, the term "crystalline microporous material of the MWW framework type" includes one or more of: a) Molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, which is incorporated by reference with respect to definitions for unit cells, building blocks, and crystal structures); b) Molecular sieves made from a common second degree building block, being a 2-dimensional tiling of such MWW framework topology unit cells, forming a monolayer of one unit cell thickness, preferably one c-unit cell thickness; c) Molecular sieves made from common second degree building blocks, being layers of one or more than one unit cell thickness, wherein the layer of more than one unit cell thickness is made from stacking, packing, or binding at least two monolayers of MWW framework topology unit cells. The stacking of such second degree building blocks can be in a regular fashion, an irregular fashion, a random fashion, or any combination thereof; and d) molecular sieves made by any regular or random 2-dimensional or 3-dimensional combination of unit cells having the MWW framework topology.

Crystalline microporous materials of the MWW framework type include those molecular sieves having an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system.

Examples of crystalline microporous materials of the MWW framework type include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), UZM-8HS (described in U.S. Pat. No. 7,713,513), UZM-37 (described in U.S. Pat. No. 7,982,084); EMM-10 (described in U.S. Pat. No. 7,842,277), EMM-12 (described in U.S. Pat. No. 8,704,025), EMM-13 (described in U.S. Pat. No. 8,704,023), MIT-1 (described by Luo et al in Chem. Sci., 2015, 6, 6320-6324), and mixtures thereof, with MCM-49 generally being preferred.

In some embodiments, the crystalline microporous material of the MWW framework type employed herein may be an aluminosilicate material having a silica to alumina molar ratio of at least 10, such as at least 10 to less than 50.

In some embodiments, the crystalline microporous material of the MWW framework type employed herein may be contaminated with other crystalline materials, such as ferrierite or quartz. These contaminants may be present in quantities of less than about 10% by weight, normally less than about 5% by weight.

The above molecular sieves may be formed into extrudates with or without another material which is resistant to the temperatures and other conditions employed in the alkylation reaction. Such materials or binders include active and inactive materials and synthetic or naturally occurring zeolites as well as inorganic materials such as clays and/or oxides such as alumina, silica, silica-alumina, zirconia, titania, magnesia, or mixtures of these and other oxides. The latter may be either naturally occurring or in the form of gelatinous precipitates or gels including mixtures of silica and metal oxides. Clays may also be included with the oxide type binders to modify the mechanical properties of the catalyst or to assist in its manufacture. Use of a material in conjunction with the molecular sieve, i.e., combined therewith or present during its synthesis, which itself is catalytically active may change the conversion and/or selectivity of the catalyst. Inactive materials suitably serve as diluents to control the amount of conversion so that products may be obtained economically and orderly without employing other means for controlling the rate of reaction. These materials may be incorporated into naturally occurring clays, e.g., bentonite and kaolin, to improve the crush strength of the catalyst under commercial operating conditions and function as binders or matrices for the catalyst. The relative proportions of molecular sieve and inorganic oxide binder may vary widely. For example, the amount of binder employed may be as little as 0 wt %, or alternatively at least 1 wt %, or at least 5 wt %, or at least 10 wt %, whereas in other embodiments the catalyst may include up to 90 wt %, for example up 80 wt %, such as up to 70 wt %, for example up to 60 wt %, such as up to 50 wt % of a binder material.

In an aspect, a solid acid catalyst can be substantially free of any binder containing amorphous alumina. As used herein, the term "substantially free of any binder containing amorphous alumina" means that the solid acid catalyst used herein contains less than 5 wt %, such as less than 1 wt %, and preferably no measurable amount, of amorphous alumina as a binder. Surprisingly, it is found that when the solid acid catalyst is substantially free of any binder containing amorphous alumina, the activity of the catalyst for isoparaffin-olefin alkylation can be significantly increased, for example by at least 50%, such as at least 75%, even at least 100% as compared with the activity of an identical catalyst but with an amorphous alumina binder.

In various aspects, the isoolefin-containing effluent can correspond to an effluent including, $C_{4+}$ isoolefins, $C_{5+}$ isoolefins, $C_{6+}$ isoolefins, $C_{7+}$ isoolefins, $C_{8+}$ isoolefins, $C_{9+}$ isoolefins, $C_{10+}$ isoolefins, $C_{11+}$ isoolefins, $C_{12}$ isoolefins, $C_4$-$C_{12}$ isoolefins, $C_6$-$C_{12}$ isoolefins, or $C_8$-$C_{12}$ isoolefins. In various aspects, the isoolefin-containing effluent can comprise 2,4,4-trimethylpent-1-ene and/or 2,4,4-trimethylpent-2-ene. In some aspects, the isoolefin-containing effluent can contain, relative to a weight of the isoolefin-containing effluent, at least about 30 wt % of isoolefins (and up to 100 wt %), or at least about 40 wt %, or at least about 50 wt %, or at least about 60 wt %, or at least about 70 wt %, or at least about 80 wt % or at least about 90 wt %, or at least about 95 wt %, or at least about 99 wt %, such as an effluent that substantially contains isoolefins (i.e., about 99.5 wt % or higher) or about 30 wt % to about 100 wt %, or about 50 wt % to about 100 wt % or about 60 wt % to about 80 wt %.

In some aspects, the isoolefin-containing effluent can contain, relative to a weight of the isoolefin-containing effluent, at least about 30 wt % of 2,4,4-trimethylpent-1-ene and/or 2,4,4-trimethylpent-2-ene (and up to 100 wt %), or at least about 40 wt %, or at least about 50 wt %, or at least about 60 wt %, or at least about 70 wt %, or at least about 80 wt % or at least about 90 wt %, or at least about 95 wt %, or at least about 99 wt %, or about 30 wt % to about 100 wt %, or about 50 wt % to about 100 wt % or about 60 wt % to about 80 wt %.

In various aspects, at least about 50% (and up to 100%) of an alcohol (e.g., tert-butyl alcohol) in the oxidation effluent can be converted to isoolefins (e.g., 2,4,4-trimethylpent-1-ene and/or 2,4,4-trimethylpent-2-ene), or at least about 60%, or at least about 70%, or at least about 80%, or at least about 90%, or at least about 95%, or at least about 99%, or about 50% to about 100%, or about 80% to about 100%, or about 90% to about 100%.

In some aspects, the isoolefin-containing effluent can comprise $C_{12}$ isoolefins, which can be hydrogenated or hydroformulated to form fluids and alcohols The composition of the alkylation effluent described herein can be dependent on the reaction conditions and the composition of the tertiary alcohol and isoparaffin feedstock(s). In any event, the product is a complex mixture of hydrocarbons, since a variety of competing reactions, such as cracking and olefin oligomerization, can also occur. In various aspects, the alkylation effluent can comprise a gasoline portion and other chemicals. As used herein, the term "gasoline" or "gasoline boiling range" refers to a composition containing at least predominantly $C_5$-$C_{12}$ hydrocarbons. In one embodiment, gasoline or gasoline boiling range components is further defined to refer to a composition containing at least predominantly $C_5$-$C_{12}$ hydrocarbons and further having a boiling range from about 100° F. to up to 330° F. In an alternative embodiment, gasoline or gasoline boiling range components is defined to refer to a composition containing at least predominantly $C_5$-$C_{12}$ hydrocarbons, having a boiling range from about 100° F. to up to 330° F., and further defined to meet ASTM standard D4814.

In various aspects, the alkylation effluent can include a $C_8$ fraction that can comprise at least about 50 wt %, such as at least about 70 wt %, of 2,3,4-, 2,3,3-, and 2,2,4-trimethylpentane relative to the weight of the $C_8$ fraction. This can correspond to an alkylate product having a higher octane value than would be obtained by a comparable process where isobutane and isobutene feeds are reacted using sulfuric acid as the catalyst. A common method for characterizing the octane rating of a composition is to use an average of the Research Octane Number (RON) and the Motor Octane Number (MON) for a composition. This type of octane rating can be used to determine the likelihood of "knocking" behavior when operating a conventional spark ignition engine. In this discussion, octane rating is defined as (RON+MON)/2, where RON is research octane number and MON is motor octane number. Although various methods are available for determining RON and MON, in the claims below, references to Research Octane Number (RON) correspond to RON determined according to ASTM D2699, while references to Motor Octane Number (MON) correspond to MON determined according to ASTM D2700.

In some aspects, a naphtha boiling range portion of the alkylation effluent can have an octane rating, as determined based on (RON+MON)/2, of at least 85, or at least 87, or at least 90, or at least 92, or at least 94, or at least 96. In particular, in some aspects the naphtha boiling range portion of the alkylation effluent can have an octane rating of about 85 to about 100, or about 90 to about 100, or about 92 to about 98, or about 92 to about 100. Additionally, in aspects where oxygenate impurities are present, for example, in the oxidation effluent, a portion of those impurities can be present in the alkylation effluent. For example, acetone generated during selective oxidation of isobutane may not be fully converted under dehydrating, dimerizing and/or hydrogenating conditions. In aspects where acetone from a selective oxidation process is included, for example, in the oxidation effluent, unconverted acetone can correspond to 0.01 mol % to 0.5 mol % of the alkylation effluent on a dry basis, or 0.05 mol % to 0.5 mol %. Dry basis refers to the hydrocarbon portion of the alkylation effluent, which excludes any water present in the alkylation effluent.

As used herein, the naphtha boiling range is defined as about 50° F. (~10° C., roughly corresponding to the lowest boiling point of a pentane isomer) to 350° F. (~177° C.). It is noted that due to practical consideration during fractionation (or other boiling point based separation) of hydrocarbon-like fractions, a fuel fraction formed according to the methods described herein may have a T5 or a T95 distillation point corresponding to the above values, as opposed to having initial/final boiling points corresponding to the above values. Compounds ($C_{4-}$) with a boiling point below the naphtha boiling range can be referred to as light ends. Optionally, a naphtha boiling range fuel composition can have a higher T5 distillation point, such as a T5 distillation point of at least about 15° C., or at least about 20° C., or at least about 30° C. In particular, a naphtha boiling range fuel composition can have a T5 to T95 distillation point range corresponding to a T5 of at least about 10° C. and a T95 of about 177° C. or less; or a T5 of at least about 15° C. and a T95 of about 177° C. or less. In the claims below, ASTM D86 should be used for determining boiling points (including fractional weight boiling points). Compounds with boiling points above 177° C. can correspond to distillate fuel boiling range compounds.

In various aspects, the dehydration and/or dimerization conditions and/or the hydrogenation conditions can include temperatures from about 100° C. to about 400° C., such as from about 100° C. to about 300° C., or about 100° C. to about 210° C. Operating temperatures can typically exceed the critical temperature of the principal component in the feed. The term "principal component" as used herein is defined as the component of highest concentration in the feedstock. For example, isobutane is the principal component in a feedstock consisting of isobutane and t-butyl alcohol in an isobutane:t-butyl alcohol molar ratio of 40:1. In some aspects, dehydration, dimerization, and/or hydrogenation temperature can be at least about 100° C., at least about 130° C., or at least about 170° C., or at least about 200° C., or at least about 250° C. Additionally or alternatively, dehydration, dimerization, and/or hydrogenation operating pressure may be from about 300 to about 1500 psig (~2.1 MPag to ~10.3 MPag), such as about 400 psig (~2.8 MPag) to about 1000 psig (6.9 MPag). Operating pressure may similarly be controlled to maintain the principal component of the feed in the supercritical state. In some aspects, the operating temperature and/or pressure can remain above the critical value for the principal feed component during the entire process run, including the first contact between fresh catalyst and fresh feed.

Hydrocarbon flow through the reaction zone containing the catalyst is typically controlled to provide an olefin liquid hourly space velocity (LHSV) sufficient to convert about 99 percent by weight of the fresh olefin to alkylate product. In some embodiments, olefin LHSV values fall within the range of about 0.01 to about 10 hr$^{-1}$. Because the conversion of tertiary alcohol to olefin in the reactor is substantially quantitative, the olefin LHSV and the tertiary alcohol LHSV can be roughly the same.

FIG. 1 shows an example of the overall reaction scheme that can be used to form alkylate from an isoparaffin feed. In FIG. 1, the isoparaffin feed is represented by isobutane. In an oxidation reaction zone and/or reaction stage, an isoparaffin feed (or a portion of such a feed) can undergo a two-step oxidation process including being exposed to selective oxidation conditions to form a hydroperoxide, such as tert-butyl hydroperoxide, in step (1) followed by decomposition of the hydroperoxide in the presence of a solid deperoxidation catalyst to an alcohol, such as tert-butyl alcohol (t-butanol) in step (2). The oxidation conditions can result in only partial conversion of the feed, so that the resulting products include a portion of unreacted isoparaffin. In addition to unreacted isoparaffin, the oxidation conditions can form t-butyl alcohol and various additional side products, such as water and acetone. This mixture from the oxidation step has been found to be an effective feed, without separation, for producing an alkylate. In a dehydration reaction zone and/or reaction stage, a mixture of unreacted isoparaffin and alcohol (and optionally at least a portion of the additional side products) can be exposed to a solid acid catalyst under controlled dehydration conditions in step (3) to form an alkene, such as isobutene. In step (4), alkenes produced in step (3) may dimerize in the presence of a solid acid catalyst to form larger olefins, such as 2,4,4-trimethylpent-1-ene and/or 2,4,4-trimethylpent-2-ene. It is contemplated herein that steps (3) and (4) may be performed in the same or different vessels or reactors. These larger olefins may then be hydrogenated in the presence of a solid acid catalyst to form isooctane in step (5). It is contemplated herein that step (5) may be performed in the same or different vessels or reactors from steps (3) and (4). The net result can be the upgrading of a low value isobutane stream to high octane blending component for gasoline.

In various aspects, an alkylate product produced according to the methods described herein is provided.

Optional Further Steps

Optional further steps for including in the hydrocarbon conversion methods are provided as well. For example, the isoparaffin-containing feed can be produced by exposing an n-paraffin-containing feed to a bifunctional acid catalyst to form the isoparaffin-containing feed via isomerization. The n-paraffin-containing feed can include $C_{4+}$ n-paraffins, $C_{5+}$ n-paraffins, $C_4$-$C_6$ n-paraffins, or $C_4$-$C_5$ n-paraffins. In some aspects, the n-paraffin-containing feed can include n-butane.

In various aspects, the oxidation effluent and/or the alkylation effluent can include unreacted n-paraffins, such as n-butane, and unreacted isoparaffins, such as isobutane. The methods described herein can further include separating a portion of unreacted n-paraffins and unreacted isoparaffins (e.g., n-butane and/or isobutane) from the alkylation effluent, for example, in a distillation column, to form a first recycle stream. Additionally or alternatively, the methods described herein can further include separating a portion of unreacted n-paraffins and unreacted isoparaffins (e.g., n-butane and/or isobutane) from the oxidation effluent, for example, in a distillation column, to form a first recycle stream. A portion of the first recycle stream and/or the second recycle stream may be recycled to n-paraffin-containing feed and/or the isoparaffin-containing feed.

Additionally or alternatively, the alkylation effluent can be, for example, conveniently fed to a separation system, such as a distillation train, to recover the $C_{9-}$ fraction for use as a gasoline octane enhancer. Depending on alkylate demand, part of all of the remaining $C_{10+}$ fraction can be recovered for use as a distillate blending stock or can be recycled to the alkylation reactor to generate more alkylate. In particular, it is found that MWW type molecular sieves are effective to crack the $C_{10+}$ fraction to produce light olefins and paraffins which can react to generate additional alkylate product and thereby increase overall alkylate yield.

III. Systems for Conversion of Hydrocarbons

Figure 2:
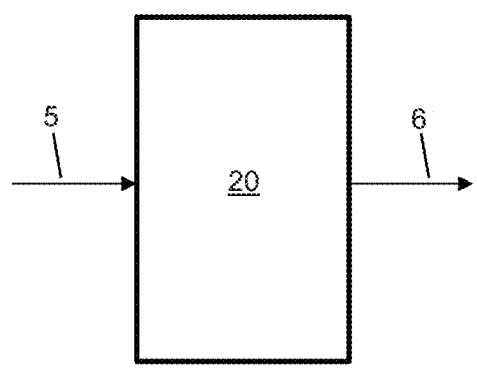
FIG. 2 schematically shows an example of a system for decomposition of a hydroperoxide to an alcohol.

FIG. 2 shows an example of a system 1 for converting hydrocarbons, such as converting hydroperoxides (such as tert-butyl hydroperoxide) to alcohol (such as tert-butyl alcohol). In FIG. 2, a hydroperoxide feed stream 5 including hydroperoxides (such as tert-butyl hydroperoxide) can be introduced into an oxidation reaction zone 20 via a hydroperoxide feed inlet (not shown). The oxidation reaction zone 20 can include a solid deperoxidation catalyst as described herein (e.g., a manganese oxide octahedral molecular sieve) for converting a portion of the hydroperoxide feed stream 5 to an oxidation effluent stream 6, for example, converting tert-butyl hydroperoxide to tert-butyl alcohol. In various aspects, the solid deperoxidation catalyst may have a selectivity of at least about 70% or at least about 90% for conversion of tert-butyl hydroperoxide to tert-butyl alcohol. In some aspects, the manganese oxide octahedral molecular sieve comprises $MnO_6$ octahedra which share edges to form a tunnel structure, for example, a 2×2 tunnel structure or a 3×3 tunnel structure. In some aspects, the solid deperoxidation catalyst may be selected from the group consisting of OMS-2, Nb-OMS-2, K-OMS-2, amorphous manganese oxide and a combination thereof. The oxidation effluent stream 6 can include an alcohol (such as tert-butyl alcohol), and the oxidation effluent stream 6 may exit the reaction zone 20 via an oxidation effluent outlet (not shown). As shown in FIG. 2, the hydroperoxide feed stream 5 and the oxidation effluent stream 6 are in fluid communication with the oxidation reaction zone 20.

Figure 3:
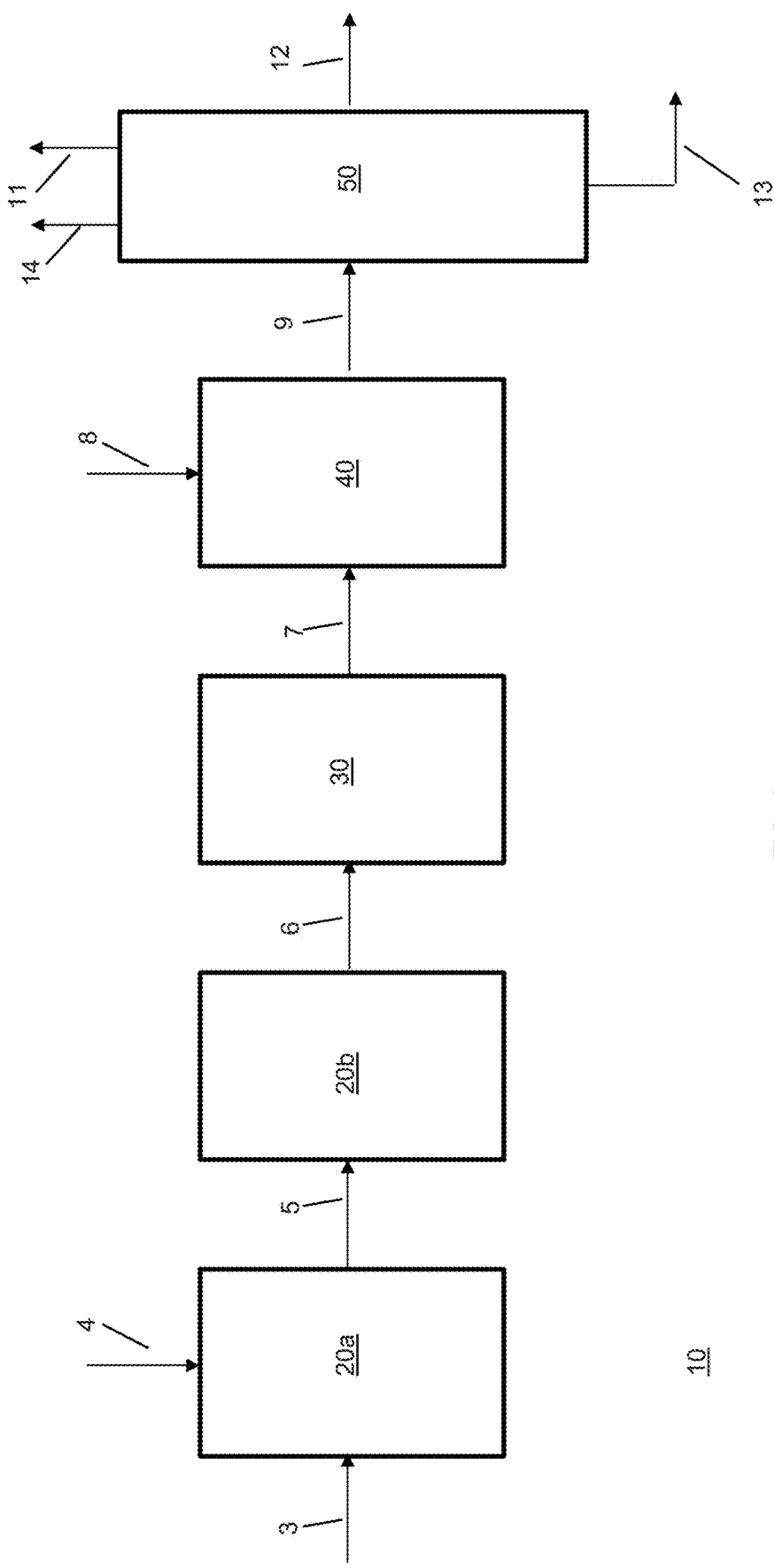
FIG. 3 schematically shows an example of a system for producing alkylate from isoparaffins.

In an alternative embodiment, as shown in FIG. 3, an oxidation reaction zone can comprise a first oxidation reactor 20a and a second oxidation reactor 20b in a system 10. An isoparaffin feed stream 3 including isoparaffins (such as isobutane) and an oxygen stream 4, such as air, can be introduced into the first oxidation reactor 20a via an isoparaffin feed inlet (not shown) and oxygen inlet (not shown), respectively. In the first oxidation reactor 20a, a portion of isoparaffins (such as isobutane) can be oxidized in the presence of oxygen under oxidation conditions as described herein to form a hydroperoxide feed stream, such as the hydroperoxide feed stream 5, which may exit the first oxidation reactor 20a via a hydroperoxide feed stream outlet (not shown). As shown in FIG. 3, the isoparaffin feed stream 3, the oxygen stream 4, and the hydroperoxide feed stream 5 are in fluid communication with the first oxidation reactor 20a.

The hydroperoxide feed stream 5 may then be introduced into a second oxidation reactor 20b via a hydroperoxide feed inlet (not shown). The second oxidation reactor 20b may comprise the solid deperoxidation catalyst as described herein for forming an oxidation effluent as described herein under decomposition conditions, such as the oxidation effluent 6, which may include an alcohol (such as tert-butyl alcohol). The oxidation effluent 6 may exit via an oxidation effluent outlet (not shown). Optionally, the oxidation effluent stream 6 can include additional oxygenates and/or other products formed during oxidation, such as methanol and/or acetone. As shown in FIG. 3, the hydroperoxide feed stream 5 and the oxidation effluent stream 6 are in fluid communication with the second oxidation reactor 20b. Although not shown, it is contemplated herein that the first oxidation reactor 20a and the second oxidation reactor 20b can be present in the same vessel or reactor.

In various aspects, the oxidation effluent stream 6 may be introduced into a dehydration and dimerization reaction zone 30 via an oxidation effluent inlet (not shown). Although not shown, it is contemplated herein that the dehydration and dimerization reaction zone may include a dehydration reactor and/or reaction stage and a dimerization reactor and/or reaction stage. The dehydration and dimerization reaction zone 30 can include a first solid acid catalyst as described herein for producing an isoolefin effluent stream 7 under dehydration and dimerization conditions as described herein. The isoolefin effluent stream 7 may exit the dehydration and dimerization reaction zone 30 via an isoolefin effluent outlet (not shown). In some aspects, the isoolefin effluent stream 7 may comprise 2,4,4-trimethylpent-1-ene and/or 2,4,4-trimethylpent-2-ene. As shown in FIG. 3, the oxidation effluent stream 6 and the isoolefin effluent stream 7 are in fluid communication with the dehydration and dimerization reaction zone 30.

In various aspects, the isoolefin effluent stream 7 and a hydrogen stream 8 may be introduced into a hydrogenation reaction zone 40 via an isoolefin effluent inlet (not shown) or via two inlets (not shown). The hydrogenation reaction zone 40 can include a second solid acid catalyst as described herein for producing an alkylation effluent stream 9 under hydrogenation conditions as described herein. The alkylation effluent stream 9 may exit the hydrogenation reaction zone 40 via an alkylation effluent outlet (not shown). In some aspects, the alkylation effluent stream 9 may comprise a $C_8$ fraction comprising at least 50 wt % of 2,3,4, 2,3,3 and 2,2,4-trimethylpentane having an octane rating, as determined by (RON+MON)/2, of at least about 90, relative to a weight of the $C_8$ fraction. As shown in FIG. 3, the isoolefin effluent stream 7, the hydrogen stream 8 and the alkylation effluent stream 9 are in fluid communication with the hydrogenation reaction zone 40. In some aspects, the dehydration and dimerization reaction zone 30 and the hydrogenation reaction zone 40 can be present in different vessels or in the same vessel as shown.

In various aspects, the first and/or second solid acid catalyst can comprise a crystalline microporous material of the MWW framework type, a mixed metal oxide, or a combination thereof. For example, the first and/or second solid acid catalyst comprises crystalline microporous material of the MWW framework type selected from the group consisting of MCM-22, PSH-3, SSZ-25, ERB-1, ITQ-1, ITQ-2, MCM-36, MCM-49, MCM-56, EMM-10, EMM-12, EMM-13, UZM-8, UZM-8HS, UZM-37, MIT-1, and a mixture thereof and optionally, an inorganic oxide binder comprising alumina, silica or a combination thereof.

In some aspects, the alkylation effluent stream 9 can be fractionated in a fractionator 50 (or other separation stage) to generate a variety of products. Optionally, a separation stage can correspond to a plurality of separators to produce desired fractions from the alkylation effluent stream 9. In the example shown in FIG. 3, the alkylation effluent stream 9 can be separated to form a water product 11, an alkylate product 12, a distillate fuels boiling range product (177° C.+) 13, and an unreacted isoparaffin stream 14 that can optionally but preferably be recycled for use as part of isoparaffin feed stream 3. Optionally, other side products in the alkylation effluent that boil below the naphtha boiling range can also be separated out (not shown).

As used herein, the term "fluid communication" refers to fluid communication, for example, between reaction zones or reactors, where a stream between reaction zones does not pass through an intervening reactor, separator, or other processing element that alters the composition of the stream, which can also be referred to as "direct fluid communication." The term "fluid communication" also encompasses fluid communication, for example, between reaction zones or reactors, where a stream can pass through one (or more) intervening processing elements between reaction zones, which can also be referred to as "indirect fluid communication."

EXAMPLES

Example 1—Preparation of Deperoxidation Catalysts

Example 1a—Preparation of Mo/C Catalyst

Mo (1 wt %) on activated carbon was synthesized by incipient wetness impregnation as follows. Ammonium molybdate tetrahydrate (739 mg $(NH_4)_6Mo_7O_{24}.4H_2O$, Sigma-Aldrich) was suspended in 4 mL of purified water and vortex-shaken at room temperature (20-25° C.) for 5 minutes until fully dissolved to form a molybdate solution. Separately, activated charcoal (Sigma-Aldrich, Darco) was dried at 110° C. for 24 h prior to use. The molybdate solution was added to 5 g of dried activated charcoal and mixed for several minutes with use of a spatula until well incorporated. The solid mixture was dried for 48 h at 110° C. under air to form the Mo/C catalyst. No further oxidative heat treatment was used.

Example 1b—Preparation of OMS-2 Catalyst

A mixture of 5.89 g of $KMnO_4$ in 100 mL of water was added dropwise (~5 mL/minute) to a solution of 8.8 g of $MnSO_4.4H_2O$ in 30 mL of water and 3 mL concentrated $HNO_3$. The solution was refluxed at 100° C. for 24 hours, and the product was filtered, washed, and dried at 120° C. to produce OMS-2. A variation of this method can involve pouring a solution of $KMnO_4$ and $Mn^{2+}$ into a Teflon-lined Parr autoclave (125 mL capacity) and heated in an oven at 100° C. for 24 h.

Example 1c—Preparation of Nb-OMS-2 Catalyst

In a 300 mL round bottom flask, a solution of $MnSO_4.H_2O$, (Sigma-Aldrich, 99+%) was prepared by dissolving the salt (8.78 g, 52 mmol) in 30 mL deionized water and 9 mL concentrated $HNO_3$ (J. T. Baker 69-70%). In a beaker, a solution of $KMnO_4$, (Sigma Aldrich, 99+%) was prepared by mixing solid potassium permanganate (4.74 g, 30 mmol) and deionized water, 100 mL. The potassium permanganate solution was added dropwise to the manganese sulfate solution while stirring. $Nb(C_2O_4H)_5.xH_2O$ (4.41 g, 8.2 mmol, Alfa Aesar) was added to the solution. The mass of metal dopant was varied depending on the desired ratios of niobium to manganese. The resulting solution after being mixed was refluxed 100-110° C. overnight. Upon cooling, the solution was filtered and washed with deionized water and then dried to 120° C. overnight to form Nb-OMS-2 catalyst. After drying, the yield of the material was 6.62 g with between 8.78 g and 4.74 g of manganese reactant. The material had a ratio of Nb:Mn of approximately 1:2.23 (i.e. about 31 mol % Nb).

Example 1d—Preparation of $Cu/Mn/Zn/Al_2O_3$ Catalyst

A Solution A was prepared by dissolving 27.3372 g of cupric nitrate trihydrate, 8.499 g of manganese(II) nitrate hydrate, 8.789 g of zinc(II) nitrate hexahydrate, and 11.037 g of aluminum nitrate nonahydrate in 300 g of $H_2O$. A Solution B was prepared by adding 1000 ml of phosphate buffer solution into a beaker. The pH of Solution B was measured as 7.0. Solution B was placed in a heated water-bath, and the temperature was maintained around 70° C. With magnetic stirring, Solution A was slowly added into Solution B, and the temperature of Solution B was maintained around 70° C. While the temperature of the mixture was maintained around 70° C., the mixture was stirred for 1 hr, and the beaker was covered with a watching glass to reduce water vaporizing. The heat was turned off of the water bath and the mixture was allowed to cool down to room temperature. The pH of the mixture was measured as 7.0. The mixture was filtered to recover the slurry, and the wet cake was washed with 500 ml of deionized $H_2O$ (di-H$_2$O) 3 times. The wet cake was re-dispersed in 500 ml di-H$_2$O. Filtering was again performed to recover the precipitates, the wet cake was washed with 500 ml of di-H$_2$O 3 times, and the wet cake was re-dispersed in 500 ml di-H$_2$O. Filtering was again performed to recover the precipitates, and the wet cake was washed with 500 ml of di-H$_2$O 3 times. The resultant catalyst was dried in air at 250° F. overnight (6-12 hours). The drying was performed as follows: the calciner was ramped at 10° F./min from room temp to 572° F. (300° C.) under air flow and remained at 572° F. (300° C.) for 3 hrs. The air flow rate was set at 5 volume/volume catalyst/minute. The catalyst was placed in a container with a plastic tape seal to prevent the sample absorb moist from air. The catalyst prepared was Cu/Mn/Zn/Al$_2$O$_3$ catalyst with the composition 60% CuO/14% MnO/16% ZnO/10% Al$_2$O$_3$—P buffer and having a Mn/Zn molar ratio=1 with the properties as shown in Table 1 below.

TABLE 1

| Catalyst | BET SA (m$^2$/g) | Pore Vol (ml/g) | Pore Size (nm) | XRD | XRF E1003 |
|---|---|---|---|---|---|
| 60% CuO/14% MnO/ 16% ZnO/10% Al$_2$O$_3$—P Buffer | 79 | 0.41 | 20.5 | X-ray amorphous | 2.53% Al, 16.72% P, 4.729% K, 0.845% Na 27.56% Cu 5.541% Mn 6.677% Zn |

Figure 4A:
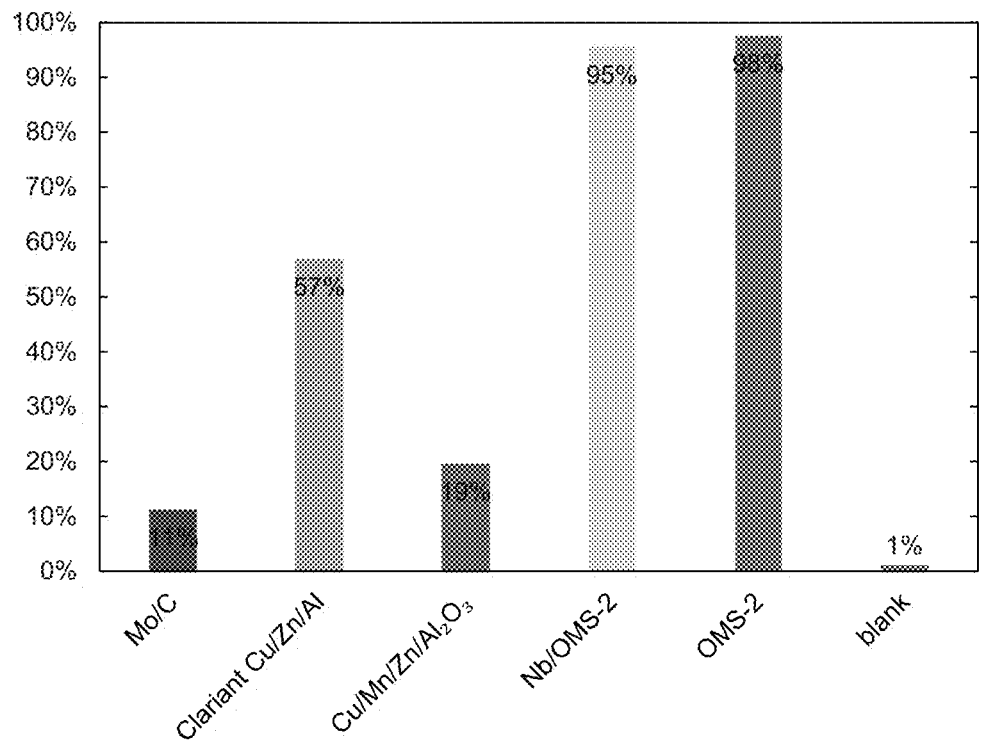
FIG. 4a shows conversion of tert-butyl hydroperoxide (TBHP) after 7 hours for various catalysts.
Figure 4B:
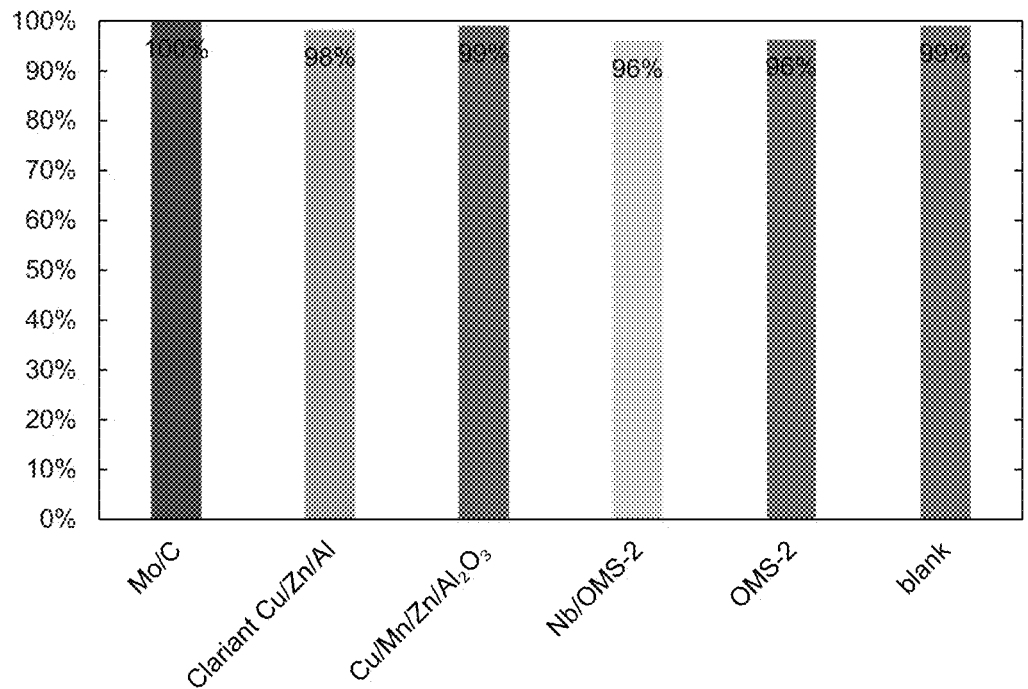
FIG. 4b shows selectivity of various catalysts for TBHP conversion to tert-butyl alcohol (TBA).
Figure 5A:
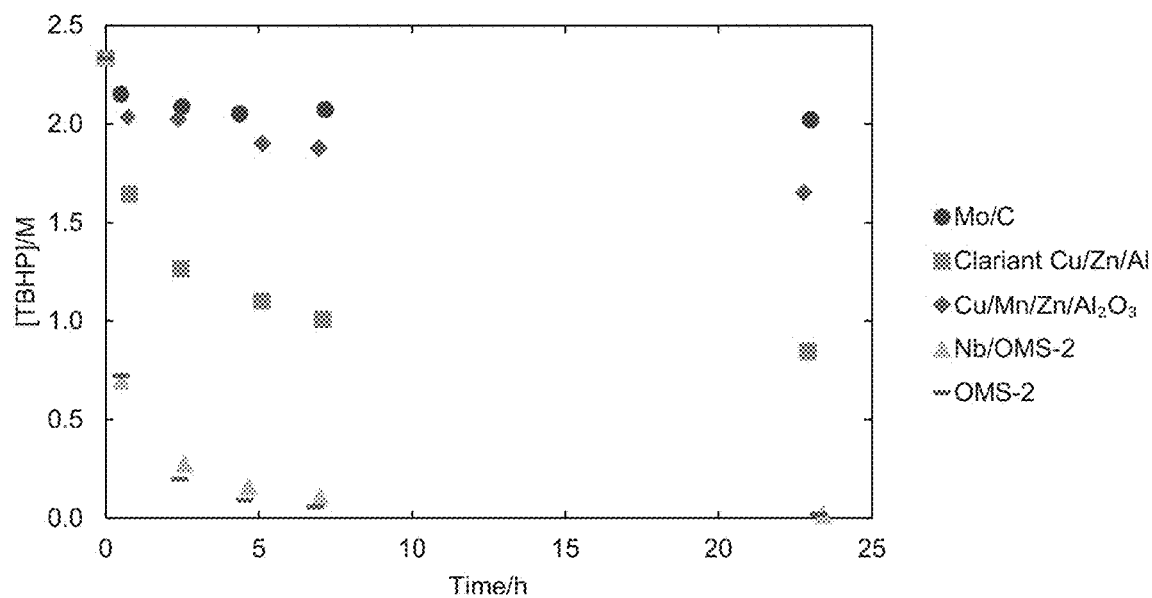
FIG. 5a shows consumption of TBHP as a function of time for various catalysts.
Figure 5B:
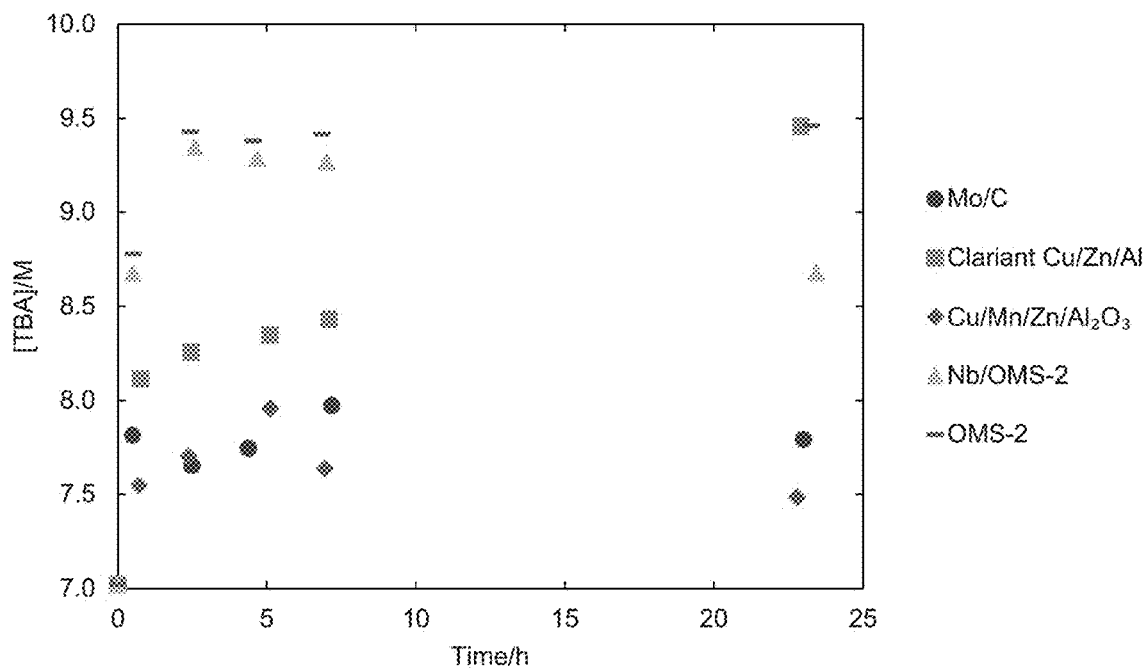
FIG. 5b shows production of TBA as a function of time for various catalysts.

Example 2—Decomposition of Tert-Butyl Hydroperoxide Use the Deperoxidation Catalysts The four catalysts prepared in Examples 1a-1d, Mo/C, OMS-2, Nb-OMS-2, and Cu/Mn/Zn/Al$_2$O$_3$, as well as Clariant Cu/Zn/Al catalyst (methanol synthesis catalysis obtained from Clariant) were tested in a hydroperoxide decomposition reaction (see step (2) in FIG. 1) using laboratory-scale batch reaction conditions (100 mg solid catalyst in 8.0 mL reaction liquid volume, stirred at 60° C. for 7 hours). The reaction medium was chosen to simulate the effluent of an autoxidation reactor (3.4 mL of 5.5 M tert-butyl hydroperoxide (TBHP) in balance decane as a model alkane diluted to 8.0 mL total volume with tert-butyl alcohol (TBA)). The results are shown in FIGS. 4a, 4b, 5a and 5b. FIG. 4a shows the conversion of TBHP after 7 hours for each of the catalysts, and FIG. 4b shows the selectivity of the catalysts for TBHP conversion to TBA calculated based on balance production of acetone after 7 hours. FIG. 5a shows consumption of TBHP as a function of time, and FIG. 5b shows production of TBA as a function of time for the catalysts.

Quantitation was performed by gas chromatography-flame ionization detector (GC-FID) using decafluorobiphenyl as an internal standard. The GC-FID was equipped with a 60 m×320 µm×1 µm Stabilwax capillary column rated for 250° C., and the autosampler carried a 10 µL syringe that was set to a 2 µL injection volume. A split ratio of 50:1 was used at the inlet, and He carrier gas was constantly flowed at a rate of 2.55 mL/min through the column. The FID was fed with 40 mL/min of H$_2$, 400 mL/min of air, and 25 mL/min of He makeup flow. For the peroxide decomposition studies, the oven temperature was initially held at 50° C. for 2 min, then ramped at 10° C./min to 208° C. and held at 208° C. for another 2 min, giving a total run time of 19.8 min.

Additional Embodiments

Embodiment 1 A method for converting hydrocarbons, comprising: an oxidizing step comprising exposing a portion of a hydroperoxide-containing feed comprising tert-butyl hydroperoxide to a solid deperoxidation catalyst under decomposition conditions (e.g., a temperature of about 50° C. to about 170° C. and a pressure of about 10 psig to about 500 psig) to form an oxidation effluent comprising tert-butyl alcohol, wherein the solid deperoxidation catalyst comprises a manganese oxide octahedral molecular sieve.

Embodiment 2 The method of embodiment 1, wherein at least about 70% or at least about 90% of the tert-butyl hydroperoxide is converted to tert-butyl alcohol and/or the solid deperoxidation catalyst has a selectivity of at least about 70% or at least about 90% for conversion of tert-butyl hydroperoxide to tert-butyl alcohol.

Embodiment 3 The method of embodiment 1 or 2, wherein the manganese oxide octahedral molecular sieve comprises MnO$_6$ octahedra which share edges to form a tunnel structure, for example, a 2×2 tunnel structure or a 3×3 tunnel structure.

Embodiment 4 The method of any one of the previous embodiments, wherein the solid deperoxidation catalyst is selected from the group consisting of OMS-2, Nb-OMS-2, K-OMS-2, OMS-1, amorphous manganese oxide and a combination thereof.

Embodiment 5 The method of any one of the previous embodiments, wherein the oxidizing step further comprises exposing an isoparaffin-containing feed comprising isobutane to oxidation conditions (e.g., a temperature of about 100° C. to about 200° C. and a pressure of about 200 psig to about 1000 psig) in the presence of oxygen to form the hydroperoxide-containing feed, wherein at least about 10 wt % of the isobutane in the isoparaffin-containing feed is converted to tert-butyl alcohol, and the isoparaffin-containing feed optionally comprises at least about 80 wt % isobutane relative to a weight of the isoparaffin-containing feed.

Embodiment 6 The method of any one of the previous embodiments, wherein a portion of the oxidation effluent further comprises water, one or more oxygenates, or a combination thereof, and the one or more oxygenates optionally comprises water, methanol, an ester, acetone, or a combination.

Embodiment 7 The method of any one of the previous embodiments, wherein the oxidation effluent comprises one or more of: a molar ratio of isobutane to tert-butyl alcohol of about 0:1 to about 2:1; a ratio by weight of tert-butyl alcohol to methanol from about 10:1 to about 25:1; and a ratio by weight of tert-butyl alcohol to acetone from about 4:1 to about 20:1, or both.

Embodiment 8 The method of any one of the previous embodiments, further comprising: a dehydrating and/or dimerizing step comprising exposing a portion of the oxidation effluent to a first solid acid catalyst under dehydrating and/or dimerizing conditions (e.g., a temperature about 100° C. to about 210° C.) to form an isoolefin-containing effluent comprising 2,4,4-trimethylpent-1-ene and/or 2,4,4-trimethylpent-2-ene, wherein at least about 70 wt % of tert-butyl alcohol is converted to 2,4,4-trimethylpent-1-ene and/or 2,4,4-trimethylpent-2-ene; and a hydrogenating step comprising exposing a portion of the isoolefin-containing effluent to a second solid acid catalyst and hydrogen under hydrogenation conditions to form an alkylation effluent comprising a C$_8$ fraction comprising at least 50 wt % of 2,3,4-, 2,3,3- and 2,2,4-trimethylpentane having an octane rating, as determined by (RON+MON)/2, of at least about 90, relative to a weight of the $C_8$ fraction, optionally wherein the first solid acid catalyst and the second solid acid catalyst are the same or different.

Embodiment 9 The method of any one of the previous embodiments, further comprising one or more of: exposing an n-paraffin-containing feed comprising n-butane to a bifunctional acid catalyst to form the isoparaffin-containing feed via isomerization; separating a portion of n-butane and/or isobutane from the alkylation effluent to form a first recycle stream; separating a portion of n-butane and/or isobutane from the oxidation effluent to form a second recycle stream; and recycling a portion of the first recycle stream and/or the second recycle stream to the n-paraffin-containing feed and/or the isoparaffin-containing feed.

Embodiment 10 The method of any one of the previous embodiments, wherein the first and/or second solid acid catalyst comprises a zeolite, a mixed metal oxide (e.g., based on oxides of Fe/W/Zr, W/Zr, Ce/W/Zr, Cu/W/Zr, Mn/W/Zr, or a combination thereof), or a combination thereof, preferably wherein the first and/or second solid acid catalyst comprises a crystalline microporous material of the MWW framework type selected from the group consisting of MCM-22, PSH-3, SSZ-25, ERB-1, ITQ-1, ITQ-2, MCM-36, MCM-49, MCM-56, EMM-10, EMM-12, EMM-13, UZM-8, UZM-8HS, UZM-37, MIT-1, and a mixture thereof; and optionally, the first and/or second solid acid catalyst further comprises an inorganic oxide binder, optionally wherein, the inorganic oxide binder comprises alumina, silica or a combination thereof.

Embodiment 11 An alkylate produce produced according to any one of the previous embodiments.

Embodiment 12 A system for conversion of hydrocarbons, comprising: a hydroperoxide feed stream comprising tert-butyl hydroperoxide and an oxidation effluent stream comprising tert-butyl alcohol, an oxidation reaction zone comprising a hydroperoxide feed inlet, an oxidation effluent outlet, and a solid deperoxidation catalyst comprising a manganese oxide octahedral molecular sieve and having a selectivity of at least about 70% for conversion of tert-butyl hydroperoxide to tert-butyl alcohol, wherein the hydroperoxide feed stream and the oxidation effluent stream are in fluid communication with the oxidation reaction zone.

Embodiment 13 The system of embodiment 12, wherein the manganese oxide octahedral molecular sieve comprises $MnO_6$ octahedra which share edges to form a tunnel structure, for example, a 2×2 tunnel structure or a 3×3 tunnel structure.

Embodiment 14 The system of embodiment 12 or 13, wherein the solid deperoxidation catalyst is selected from the group consisting of OMS-2, Nb-OMS-2, K-OMS-2, OMS-1, amorphous manganese oxide and a combination thereof.

Embodiment 15 The system of any one of embodiments 12 to 14, further comprising an isoparaffin feed stream comprising isobutane and an oxygen stream, wherein the oxidation reaction zone further comprise a first oxidation reactor comprising an isoparaffin feed inlet, an oxygen inlet, and a hydroperoxide feed stream outlet, wherein the isoparaffin feed stream, the oxygen stream, and the hydroperoxide feed stream are in fluid communication with the first oxidation reactor, a second oxidation reactor comprising the solid deperoxidation catalyst, the hydroperoxide feed inlet, and the oxidation effluent outlet, wherein the hydroperoxide feed stream and the oxidation effluent stream are in fluid communication with the second oxidation reactor.

Embodiment 16 The system of any one of embodiments 12 to 15, further comprising an isoolefin effluent stream comprising 2,4,4-trimethylpent-1-ene and/or 2,4,4-trimethylpent-2-ene, a dehydration and dimerization reaction zone comprising an oxidation effluent inlet, an isoolefin effluent outlet, and a first solid acid catalyst comprising a crystalline microporous material of the MWW framework type, a mixed metal oxide, or a combination thereof, wherein the oxidation effluent stream and the isoolefin effluent stream are in fluid communication with the dehydration and dimerization reaction zone, a hydrogen stream, an alkylation effluent stream comprising a $C_8$ fraction comprising at least 50 wt % of 2,3,4, 2,3,3 and 2,2,4-trimethylpentane having an octane rating, as determined by (RON+MON)/2, of at least about 90, relative to a weight of the $C_8$ fraction, a hydrogenation zone comprising an isoolefin effluent inlet, an alkylation effluent outlet, and a second solid acid catalyst comprising a crystalline microporous material of the MWW framework type, a mixed metal oxide, or a combination thereof, wherein the isoolefin effluent stream, the hydrogen stream, and the alkylation effluent stream are in fluid communication with the hydrogenation reaction zone, optionally wherein the dehydration and dimerization reaction zone and the hydrogenation reaction zone are present in different vessels or in the same vessel.

Embodiment 17 The system of any one of embodiments 12 to 16, wherein the first and/or second solid acid catalyst comprises crystalline microporous material of the MWW framework type selected from the group consisting of MCM-22, PSH-3, SSZ-25, ERB-1, ITQ-1, ITQ-2, MCM-36, MCM-49, MCM-56, EMM-10, EMM-12, EMM-13, UZM-8, UZM-8HS, UZM-37, MIT-1, and a mixture thereof and optionally, an inorganic oxide binder comprising alumina, silica or a combination thereof.

When numerical lower limits and numerical upper limits are listed herein, ranges from any lower limit to any upper limit are contemplated. While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

The present invention has been described above with reference to numerous embodiments and specific examples. Many variations will suggest themselves to those skilled in this art in light of the above detailed description. All such obvious variations are within the full intended scope of the appended claims.

The invention claimed is:

1. A method for converting hydrocarbons, comprising:
    an oxidizing step comprising exposing a portion of a hydroperoxide-containing feed comprising tert-butyl hydroperoxide to a solid deperoxidation catalyst under decomposition conditions to form an oxidation effluent comprising tert-butyl alcohol, wherein the decomposition conditions comprise a temperature of about 50° C. to about 170° C. and a pressure of about 10 psig to about 500 psig, wherein the solid deperoxidation catalyst comprises a manganese oxide octahedral molecular sieve, wherein the manganese oxide octahedral molecular sieve comprises a $MnO_6$ octahedra which share edges to form a tunnel structure, wherein the oxidizing step further comprises exposing an isoparaffin-containing feed comprising isobutane to oxidation conditions in the presence of oxygen to form the hydroperoxide-containing feed, wherein at least about 10 wt % of the isobutane in the isoparaffin-containing feed is converted to tert-butyl alcohol, and the isoparaffin-containing feed optionally comprises at least about 80 wt % isobutane relative to a weight of the isoparaffin-containing feed, wherein the oxidation conditions comprise a temperature of about 100° C. to about 200° C. and a pressure of about 200 psig to about 1000 psig;

a dehydrating and/or dimerizing step comprising directly exposing a portion of the oxidation effluent to a first solid acid catalyst under dehydrating and/or dimerizing conditions to form an isoolefin-containing effluent comprising 2,4,4-trimethylpent-1-ene and/or 2,4,4-trimethylpent-2-ene, wherein at least about 70 wt % of tert-butyl alcohol is converted to 2,4,4-trimethylpent-1-ene and/or 2,4,4-trimethylpent-2-ene; and a hydrogenating step comprising directly exposing a portion of the isoolefin-containing effluent to a second solid acid catalyst and hydrogen under hydrogenation conditions to form an alkylation effluent comprising a $C_8$ fraction comprising at least 50 wt % of 2,3,4-, 2,3,3- and 2,2,4-trimethylpentane having an octane rating, as determined by (RON+MON)/2, of at least about 90, relative to a weight of the $C_8$ fraction, wherein the first solid acid catalyst and the second solid acid catalyst are the same or different.

2. The method of claim 1, wherein at least about 70% of the tert-butyl hydroperoxide is converted to tert-butyl alcohol and/or the solid deperoxidation catalyst has a selectivity of at least about 70% for conversion of tert-butyl hydroperoxide to tert-butyl alcohol.

3. The method of claim 1, wherein at least about 90% of the tert-butyl hydroperoxide is converted to tert-butyl alcohol and/or the solid deperoxidation catalyst has a selectivity of at least about 90% for conversion of tert-butyl hydroperoxide to tert-butyl alcohol.

4. The method of claim 1, wherein the tunnel structure is 2×2 tunnel structure or 3×3 tunnel structure.

5. The method of claim 1, wherein the solid deperoxidation catalyst is selected from the group consisting of OMS-2, Nb-OMS-2, K-OMS-2, OMS-1, amorphous manganese oxide and a combination thereof.

6. The method of claim 1, wherein the oxidation effluent comprises a molar ratio of isobutane to tert-butyl alcohol of about 0:1 to about 2:1.

7. The method of claim 1, wherein a portion of the oxidation effluent further comprises water, one or more oxygenates, or a combination thereof, and the one or more oxygenates optionally comprises water, methanol, an ester, acetone, or a combination.

8. The method of claim 7, wherein the ratio by weight of tert-butyl alcohol to methanol in the oxidation effluent is from about 10:1 to about 25:1, the ratio by weight of tert-butyl alcohol to acetone is from about 4:1 to about 20:1, or both.

9. The method of claim 1, further comprising one or more of:
exposing an n-paraffin-containing feed comprising n-butane to a bifunctional acid catalyst to form the isoparaffin-containing feed via isomerization;
separating a portion of n-butane and/or isobutane from the alkylation effluent to form a first recycle stream;
separating a portion of n-butane and/or isobutane from the oxidation effluent to form a second recycle stream; and
recycling a portion of the first recycle stream and/or the second recycle stream to the n-paraffin-containing feed and/or the isoparaffin-containing feed.

10. The method of claim 1, wherein the first and/or second solid acid catalyst comprises a zeolite, a mixed metal oxide, or a combination thereof.

11. The method of claim 1, wherein the first and/or second solid acid catalyst comprises a crystalline microporous material of the MWW framework topology selected from the group consisting of MCM-22, PSH-3, SSZ-25, ERB-1, ITQ-1, ITQ-2, MCM-36, MCM-49, MCM-56, EMM-10, EMM-12, EMM-13, UZM-8, UZM-8HS, UZM-37, MIT-1, and a mixture thereof.

12. The method of claim 1, wherein the first and/or second solid acid catalyst comprises a mixed metal oxide based on oxides of Fe/W/Zr, W/Zr, Ce/W/Zr, Cu/W/Zr, Mn/W/Zr, or a combination thereof.

13. The method of claim 1, wherein the first and/or second solid acid catalyst further comprises an inorganic oxide binder, optionally wherein, the inorganic oxide binder comprises alumina, silica or a combination thereof.

14. The method of claim 1, wherein the dehydrating and/or dimerizing conditions comprise a temperature about 100° C. to about 210° C.

* * * * *